US007950388B2

(12) United States Patent
Kunze et al.

(10) Patent No.: US 7,950,388 B2
(45) Date of Patent: May 31, 2011

(54) NEBULISER AND CONTAINER

(75) Inventors: Hubert Kunze, Dortmund (DE); Matthias Hausmann, Rees (DE); Jens Besseler, Dortmund (DE); Carsten Henning, Recklinghausen (DE); Heinrich Kladders, Muelheim (DE); Florian Witte, Schwabenheim (DE); Johannes Geser, Ingelheim (DE); Markus Mast, Biel (CH); Antonino Lanci, Bern (CH); Christoph Dworzak, Biel (CH); Elmar Mock, Colombier (CH)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 690 days.

(21) Appl. No.: 11/426,406

(22) Filed: Jun. 26, 2006

(65) Prior Publication Data

US 2007/0090205 A1 Apr. 26, 2007

(30) Foreign Application Priority Data

Jun. 24, 2005 (DE) ......................... 10 2005 029 746

(51) Int. Cl.
*A61M 11/00* (2006.01)

(52) U.S. Cl. ......... 128/200.14; 128/200.22; 222/189.09; 222/189.11

(58) Field of Classification Search .................. 239/309, 239/318, 320, 321, 329, 333, 338, 339, 340, 239/347, 348, 349, 355; 222/383.1, 385, 222/401, 189.09, 189.1, 464.6, 464.2, 464.1, 222/386, 380, 402, 189.11; 128/200.22, 128/200.14
See application file for complete search history.

(56) References Cited

U.S. PATENT DOCUMENTS

| | | | | |
|---|---|---|---|---|
| 2,272,943 | A * | 2/1942 | Healy | 239/362 |
| 3,746,261 | A * | 7/1973 | Nozawa et al. | 239/333 |
| 3,799,448 | A * | 3/1974 | Nozawa et al. | 239/321 |
| 4,195,730 | A * | 4/1980 | Hunt | 206/221 |
| 4,264,018 | A | 4/1981 | Warren | |
| 4,817,830 | A | 4/1989 | Yavorsky | |
| 5,176,178 | A | 1/1993 | Schurter et al. | |
| 5,242,085 | A | 9/1993 | Richter et al. | |
| 5,295,603 | A * | 3/1994 | Schormair et al. | 220/789 |
| 5,332,121 | A | 7/1994 | Schmidt et al. | |
| 5,334,178 | A * | 8/1994 | Haber et al. | 604/415 |
| 5,642,838 | A * | 7/1997 | Stoody | 222/83 |
| 5,657,909 | A * | 8/1997 | Barriac | 222/382 |
| 5,662,271 | A | 9/1997 | Weston et al. | |
| 5,752,629 | A | 5/1998 | Hardy | |
| 5,833,088 | A | 11/1998 | Kladders et al. | |
| 5,944,217 | A | 8/1999 | Baena | |
| 5,971,221 | A * | 10/1999 | Schwarz | 222/189.09 |
| 6,129,236 | A | 10/2000 | Osokin et al. | |

(Continued)

FOREIGN PATENT DOCUMENTS

DE 3446697 A1 6/1986

(Continued)

*Primary Examiner* — Steven O Douglas
(74) *Attorney, Agent, or Firm* — Roberts Mlotkowski Safran & Cole, P.C.; David S. Safran

(57) ABSTRACT

A nebuliser and a container in each case with an aeration device are proposed, the aeration device being designed for the direct aeration of a liquid space in the container. The container comprises a rigid, gas-tight outer case and a closure, which is opened by connecting or inserting a delivery element. A long storage life and long service life with low loss of fluid or solvent are thereby provided in the form of a simple and inexpensive construction.

56 Claims, 24 Drawing Sheets

U.S. PATENT DOCUMENTS

| | | | |
|---|---|---|---|
| 6,223,933 | B1 | 5/2001 | Hochrainer et al. |
| 6,244,472 | B1 * | 6/2001 | Hennemann ............. 222/189.09 |
| 6,250,508 | B1 * | 6/2001 | Geser et al. ................ 222/189.1 |
| 6,726,124 | B2 | 4/2004 | Jaeger et al. |
| 6,918,547 | B2 | 7/2005 | Jaeger et al. |
| 6,971,553 | B2 * | 12/2005 | Brennan et al. ............... 222/207 |
| 2004/0045548 | A1 * | 3/2004 | Hochrainer .............. 128/200.14 |
| 2004/0069812 | A1 | 4/2004 | Beranger et al. |

FOREIGN PATENT DOCUMENTS

| | | | |
|---|---|---|---|
| DE | 4427354 | A1 | 2/1996 |
| DE | 19729117 | A1 | 1/1999 |
| EP | 0376629 | A2 | 7/1990 |
| EP | 0377067 | A1 | 7/1990 |
| EP | 0379047 | A1 | 7/1990 |
| EP | 0380934 | A1 | 8/1990 |
| EP | 0388696 | A1 | 9/1990 |
| EP | 0439109 | A2 | 7/1991 |
| EP | 0461065 | A1 | 12/1991 |
| EP | 0500249 | A1 | 8/1992 |
| EP | 0517121 | A2 | 12/1992 |
| EP | 0525842 | A2 | 2/1993 |
| EP | 0610715 | A1 | 8/1994 |
| EP | 0754630 | A1 | 1/1997 |
| EP | 0812625 | A2 | 12/1997 |
| EP | 085687 | A1 | 8/1998 |
| EP | 1202616 | A1 | 5/2002 |
| EP | 1334916 | A1 | 8/2003 |
| FR | 2820408 | A1 | 8/2002 |
| GB | 2132989 | A | 7/1984 |
| GB | 2202836 | A | 10/1988 |
| WO | 94 12411 | A1 | 6/1994 |
| WO | 94 15159 | A1 | 7/1994 |
| WO | 97 15378 | A1 | 5/1997 |
| WO | 99 02211 | A1 | 1/1999 |
| WO | 99 26001 | A1 | 5/1999 |
| WO | 00 27543 | A1 | 5/2000 |
| WO | 0029297 | A1 | 5/2000 |
| WO | 00 48921 | A1 | 8/2000 |
| WO | 02 074651 | A2 | 9/2002 |
| WO | 2004065247 | A1 | 8/2004 |

* cited by examiner

NEBULISER AND CONTAINER

BACKGROUND OF THE INVENTION

1. Field of the Invention

The present invention relates to a nebuliser for a fluid, with a preferably insertable container with a fluid space for the fluid as well as a container for a nebuliser.

2. Description of Related Art

A nebuliser available under the trademark RESPIMAT® in the form of an inhaler is known, and is illustrated in its basic form in International Patent Application Publication WO 91/14468 A1 (U.S. Pat. No. 5,662,271) and in a specific configuration in International Patent Application Publication WO 97/12687 A1 (U.S. Pat. Nos. 6,918,547 and 6,726,124) as well as in FIGS. 1 & 2 of the accompanying drawings. The nebuliser has, as a reservoir for a fluid to be atomized, an insertable rigid container with a deflatable inner bag containing the fluid and a pressure generator with a drive spring for delivering and atomizing the fluid.

Before the nebuliser is used for the first time, it is opened by loosening a lower housing part, and the sealed container is inserted into the nebuliser. The container is opened by a delivery tube that is introduced into the container as far as the inner bag when the said container is inserted. The lower housing part is then slipped on again.

The drive spring can be tensioned by rotating the lower housing part of the nebuliser. During the tensioning (priming) the container within the nebuliser is moved in a stroke-like manner into the lower housing part and fluid is sucked from the inner bag into a pressure chamber of the pressure generator. After manual actuation of a locking element the fluid in the pressure chamber is pressurized by the drive spring and discharged by means of the delivery tube and without propellant gas through a nozzle into a mouthpiece as an aerosol.

The container comprises an aeration device on the base side, which is pierced during the initial tensioning of the nebuliser and is thereby permanently opened. The aeration device serves to aerate the container so that the inner bag can deflate when fluid is removed, without a reduced pressure thereby being produced in the bag.

International Patent Application Publication WO 00/27543 A1 (U.S. Pat. No. 6,223,933), which forms the starting point of the present invention, discloses various aeration and pressure compensation devices for such a container with a debatable inner bag. The devices serve to provide only a slow pressure compensation between the ambient atmosphere and the gas space between the inner bag and the rigid outer case of the container.

SUMMARY OF THE INVENTION

A primary object of the present invention is to provide a nebuliser and a container that is of simple construction and is easy and inexpensive to produce, wherein pressure compensation is possible between the fluid contained in the interior of the rigid container and the surroundings.

The above object is achieved by a nebuliser in accordance with the present invention in which the aeration device is designed for the direct aeration of the fluid space in the container. The fluid space within the meaning of the present invention is the space formed by the container and accommodating the fluid, or a gas space in the container that is in direct contact therewith. In particular, the fluid is filled directly into the outer case of the container or is in contact therewith. A debatable inner bag is not provided. The result is thus a simple and inexpensive construction.

The aeration device is preferably designed in such a way that an excessive evaporation of the fluid, in particular, of a solvent of the fluid, is avoided. For this purpose, the aeration device preferably comprises a channel that, on the one hand, permits rapid pressure compensation, and on the other hand, forms an effective barrier to minimize evaporation. Alternatively or in addition, the aeration device is preferably designed in such a way that it is opened only temporarily, in particular, by or during a movement involving removal of fluid, delivery of fluid, pressure generation and/or atomization.

The solution according to the invention of the invention provides a substantially simpler construction, since a deflatable inner bag is not necessary and is not provided. The aeration device in fact allows direct pressure compensation between the fluid space formed by the rigid container, and the surroundings. Pressure compensation is necessary, in particular, when withdrawing fluid, in temperature changes and/or changes of the ambient pressure. Due to the direct aeration of the fluid space in the container, there is a direct gas connection between the fluid and the surroundings when the aeration device is open, with the result that a quicker pressure compensation is possible. In particular, the aeration takes place via a flow pathway different from that involved in the withdrawal of fluid from the container, in order to be able to prevent, by simple means, entrainment of gas bubbles when fluid is withdrawn.

Further advantages, features, properties and aspects of the present invention are disclosed in the following detailed description of preferred embodiments in conjunction with the accompanying drawings.

DETAILED DESCRIPTION OF THE INVENTION

Figure 1:
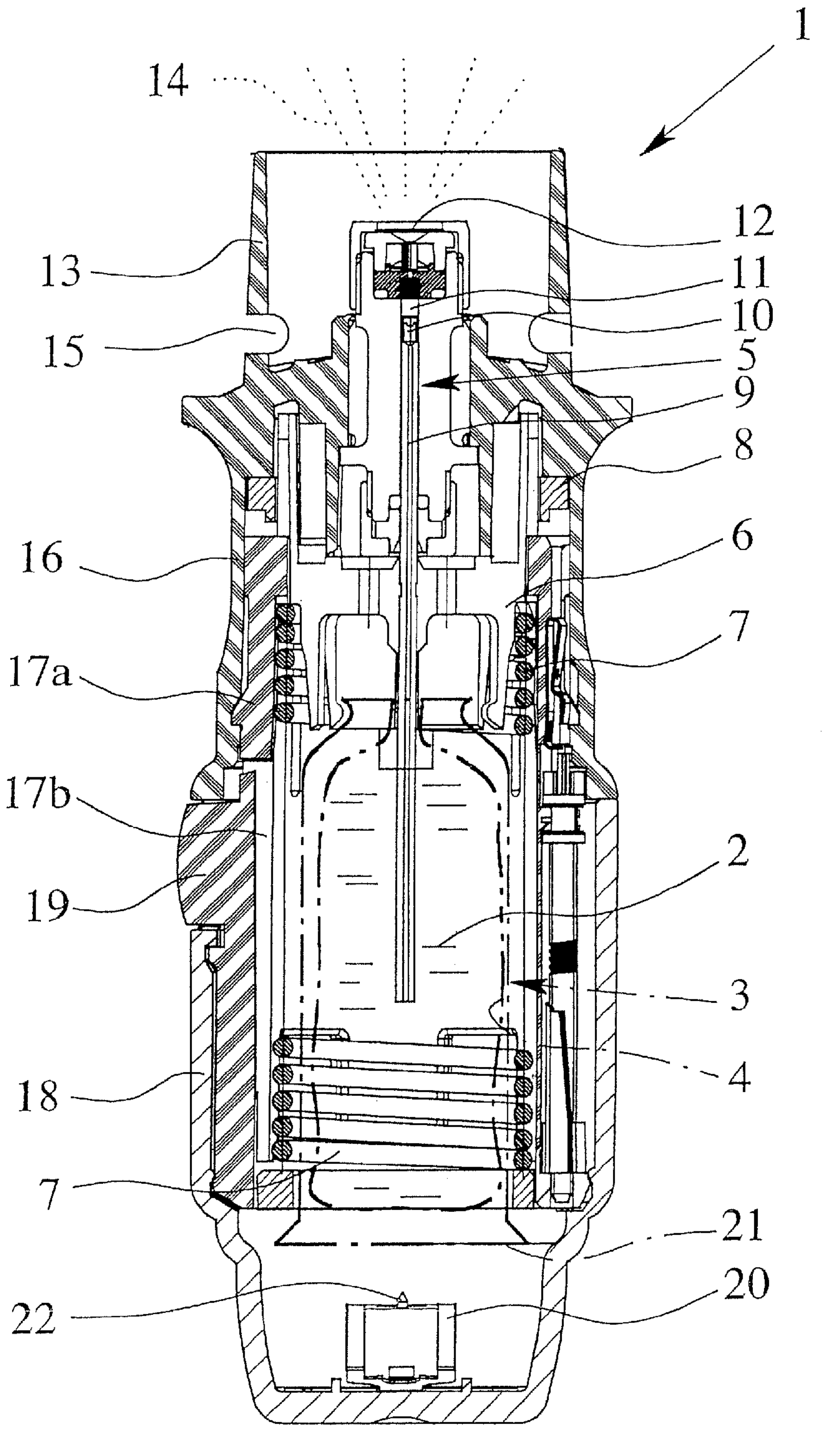
FIG. 1 is a diagrammatic sectional view of a known nebuliser in the untensioned state.

In the figures, the same reference numerals are used for identical or similar parts where corresponding or comparable properties and advantages are obtained, even if a relevant description is omitted.

Figure 2:
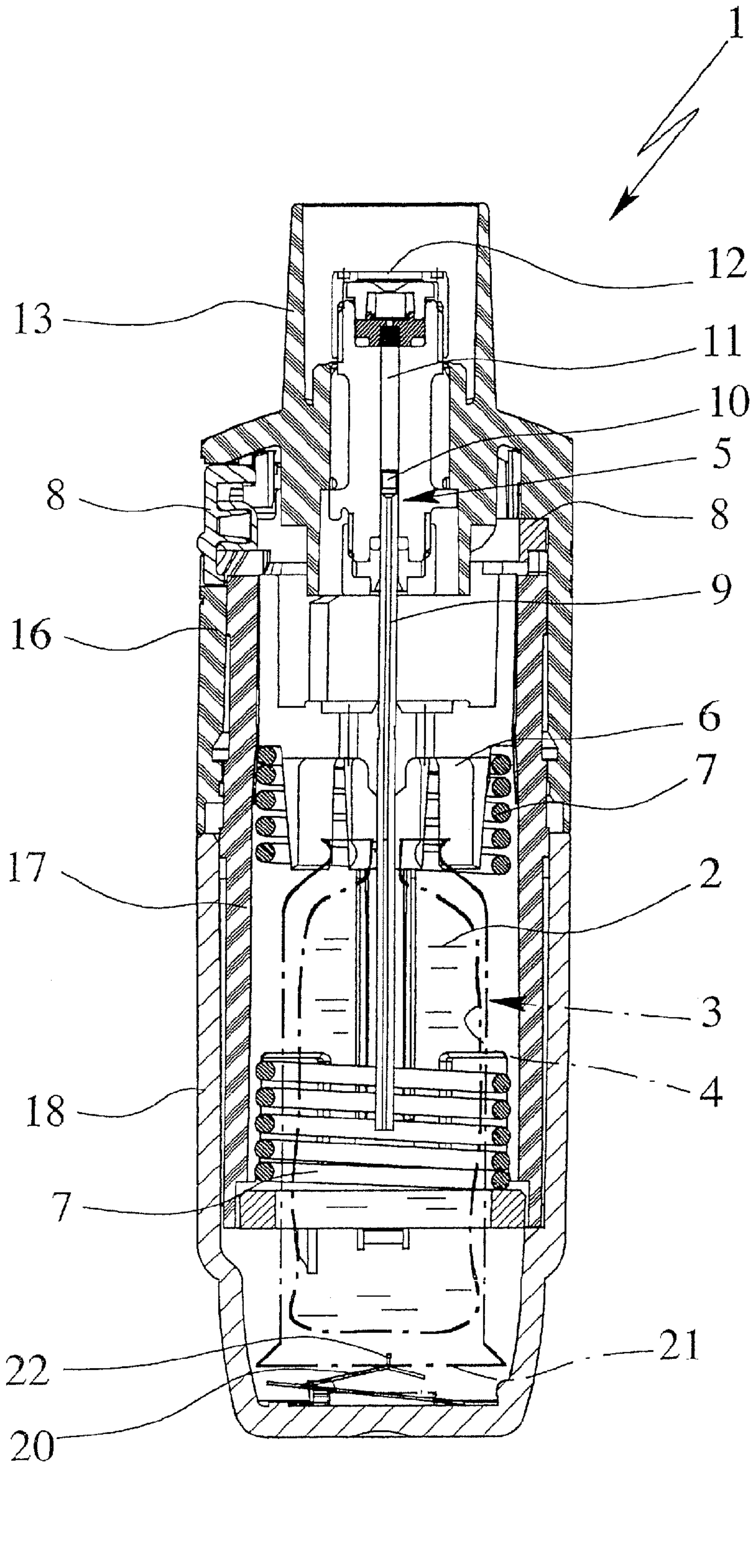
FIG. 2 is a diagrammatic sectional view of the known nebuliser in the tensioned state, rotated by 90° relative to the view in FIG. 1.

FIGS. 1 & 2 show a known nebuliser 1 for atomizing a fluid 2, in particular, a highly active medicament or the like, in a diagrammatic representation in the untensioned state (FIG. 1) and tensioned state (FIG. 2). The nebuliser is designed, in particular, as a portable inhaler, and preferably, operates without propellant gas.

On atomization of the fluid 2, preferably a liquid, in particular, a medicament, an aerosol is formed that can be breathed in or inhaled by a user (not shown). Normally inhalation is performed at least once a day, in particular, several times a day, preferably, at predetermined time intervals, depending on the patient's medical condition.

The known nebuliser 1 comprises an insertable and preferably replaceable container 3 with the fluid 2. The container 3 thus forms a reservoir for the fluid 2 to be atomized. The container 3 preferably contains a sufficient amount of fluid 2 or active substance in order, for example, to be able to provide up to 200 dose units, i.e., to permit, for example, up to 200 atomizations or uses. A typical container 3, as is disclosed in International Patent Application Publication No. WO 96/06011 A2 (U.S. Pat. No. 5,833,088), accommodates a volume of ca. 2 to 10 ml.

The container 3 is substantially cylindrical or like a cartridge, and after the opening of the nebuliser 1, can be inserted into it, and optionally, replaced. The container is of rigid construction, the fluid 2 being accommodated in the container 3 in a fluid space 4 formed by a deflatable bag.

Furthermore, the nebuliser 1 comprises a pressure generator 5 for delivering and atomizing the fluid 2, in particular, in each case, in a predetermined and optionally adjustable dose amount. The pressure generator 5 has a holder 6 for the container 3, an associated and only partly-shown drive spring 7 with a manually actuatable locking element 8 for unlocking purposes, a delivery tube 9 with a non-return valve 10, a pressure chamber 11 and a delivery nozzle 12 in the region of a mouthpiece 13. The container 3 is fixed via the holder 6, in particular, in a notched manner, in the nebuliser 1, so that the delivery tube 9 dips into the container 3. In this connection, the holder 6 may be designed so that the container 3 can be released and exchanged.

When the drive spring 7 is axially tensioned, the holder 6 together with the container 3 and the delivery tube 9 shown in the drawings is moved downwards and fluid 2 is suctioned from the container 3 through the non-return valve 10 into the pressure chamber 11 of the pressure generator 5.

During the subsequent release of tension after actuating the locking element 8, the fluid 2 in the pressure chamber 11 is pressurized, wherein the delivery tube 9 together with its now closed non-return valve 10 is moved upwardly again due to release of tension on the drive spring 7, and now serves as a plunger. This pressure forces the fluid 2 through the discharge nozzle 12, whereby it is atomized to form an aerosol 14, as illustrated in FIG. 1.

A user or patient (not shown) can inhale the aerosol 14, whereby air can be sucked into the mouthpiece 13 through at least one air feed opening 15.

The nebuliser 1 comprises an upper housing part 16 and an inner part 17 rotatable relative thereto (FIG. 2) together with an upper part 17*a* and a lower part 17*b* (FIG. 1), wherein, in particular, a manually actuatable housing part 18 is releasably secured to, in particular, mounted on, the inner part 17, preferably, by means of a holding element 19.

The housing part 18 may be rotated relative to the upper housing part 16, whereby it engages the lower part 17*b* of the inner part 17, as shown in the drawing. In this way, the drive spring 7 is tensioned in the axial direction via a gear mechanism (not shown) acting on the holder 6. As a result of the tensioning, the container 3 is moved axially downwards until the container 3 adopts an end position illustrated in FIG. 2. In this state, the drive spring 7 is tensioned. During the initial tensioning, an axially acting spring 20 arranged in the housing part 18 comes to bear on the container base 21 and pierces the container 3 or a seal on the base with a piercing element 22 when the container initially makes contact, to allow air in. During the atomization procedure, the container 3 is retracted by the drive spring 7 to its starting position. Thus, the container 3 executes a reciprocating movement during the tensioning procedure and for removal of fluid and during the atomization procedure.

The design, construction and mode of operation of several embodiments of the proposed nebuliser 1 and container 3 are describe in more detail hereinafter, reference being made to further figures, though only essential differences compared to the nebuliser 1 and container 3 according to FIGS. 1 & 2 are emphasized. The descriptions given with respect to FIGS. 1 & 2 thus apply correspondingly or in a supplementary way, and arbitrary combinations of features of the nebuliser according to FIGS. 1 & 2 and of the nebulisers 1 and containers 3 according to the embodiments described hereinafter or with one another are also possible.

Figure 3:
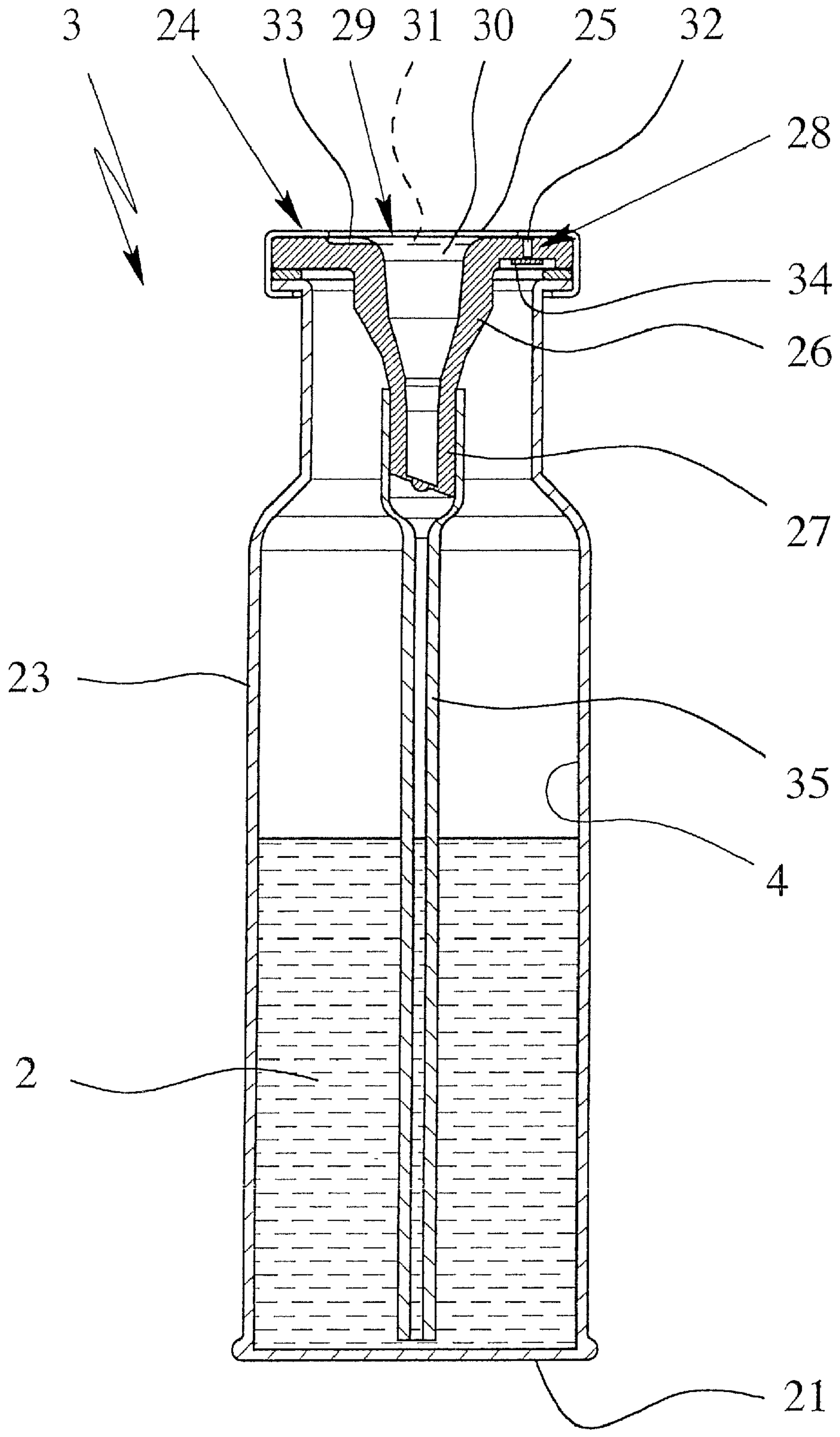
FIG. 3 is a diagrammatic sectional view of a proposed container according to a first embodiment.

FIG. 3 is a diagrammatic sectional view of the proposed container 3 according to a first embodiment in the closed state without the associated nebuliser 1.

The container 3 comprises a rigid, gas-tight outer case 23. The term "gas-tight" is understood in the context of the present invention to mean that a diffusion of the fluid 2 or at least of an essential constituent of the fluid 2, such as a solvent, for example, water or ethanol, is not possible or is prevented. Therefore, the outer case 23 is, in this respect, at least substantially impermeable. Furthermore, the term "gas-tight" is basically understood to mean that air or other gas cannot penetrate through the outer case 23 for the purposes of pressure compensation.

Preferably, the outer case 23 is made of glass, metal or another suitable, gas-tight plastics, such as COC (cyclopolyolefin polymer) in order to achieve the desired hermeticity. In addition or alternatively, the outer case 23 can also be fabricated from a composite material, for example, with an inner lamination of plastics, inner coating, or the like.

The container 3 does not have a deflatable bag or the like. Instead, the fluid 2 is filled directly into the outer case 23 and is in contact therewith. The outer case 23 forms the fluid space 4 for the fluid 2, the said space consequently being rigid.

Preferably the container 3 is fabricated as a single-walled structure, i.e., without a bag, inner case or the like. The outer case 23 is, preferably, formed as a single layer, though it may also be fabricated from several layers, if necessary.

The container 3 comprises a closure 24 that seals the container 3 in a gas-tight manner, preferably after the latter has been filled with the fluid 2. The closure 24 is preferably mounted on the front or top of the container 3 or on its outer case 23.

The seal 24 preferably comprises an outer cover or seal 25 and a cap or insert 26 arranged thereunder. In order to achieve the desired hermeticity, which is essential for a long storage life, particularly when the container 3 is sealed, the cover or seal 25, which made, in particular, of a metal foil, is formed so as to be gas tight. Preferably, the insert 26 is inserted into the container 3 together with the metal film and is hot-sealed, in order to achieve the desired hermeticity. In addition or alternatively, the insert 26, and optionally the seal 25, may be secured and fastened by crimping a metal ring or the like on the top of the container.

According to a modified embodiment (not shown), the cover or seal 25 may also be formed by a protective cap or the like that is welded on, bonded on or secured in another suitable way.

Preferably the seal 25 forms an original closure of the container 3.

Furthermore, the container 3 comprises a sealing element 27 arranged in the interior, such as a septum, a membrane or the like, shown only partly in the figures. The sealing element 27 is preferably formed by the closure 24 or insert 26 and serves in particular, to radially seal an inserted delivery element, in particular, the delivery tube 9 or the like, which is not shown in FIG. 3.

In order to extract fluid 2 the container 3 is inserted into the nebuliser 1, and in particular, is opened by connecting or introducing the delivery element, i.e., in this case, the delivery tube 9. In particular, the delivery tube 9 pierces the seal 25 and is introduced into the sealing element 27 or is possibly even forced through the latter, in order to produce a fluid connection to the fluid 2 in the container 3. The introduction of the delivery tube 9 thus, preferably, leads to an opening of the container 3, in particular, of the seal 25 and of the closure 24. However, the opening may alternatively also take place independently of the removal of fluid and/or independently of the delivery element, in particular, by means of a separate part or the like (not shown).

According to the invention, an aeration device 28 is provided for the preferably direct aeration of the fluid space 4 in the container 3. Thus, the aeration device 28, preferably, forms a direct gas connection between the fluid 2 and the surroundings when the aeration device 28 is open, in order to allow the pressure compensation already mentioned in the introduction.

In the first embodiment the aeration device 28 is integrated into the closure 24 or at least forms a part thereof and/or is arranged thereon. However, the aeration device 28 may, in principle, also be arranged and/or formed on the nebuliser 1, in particular, separately from the container 3 as is also explained hereinafter with the aid of other embodiments.

In the first embodiment, the aeration device 28 includes a flow channel or throttle channel, which hereinafter is briefly denoted as channel 29 and can be seen more clearly in the enlargement of the insert 26 according to FIG. 4.

The channel 29 is configured so that it produces a relatively low flow resistance with regard to a rapid pressure compensation—in particular, in the case of rapid successive withdrawal of fluid 2 from the container 3. However, the channel 29 forms a barrier to the evaporation or diffusion of the fluid 2, in particular, of constituents of the fluid 2 such as a solvent, for example, water or ethanol, that is relatively difficult to overcome. The evaporation or diffusion and the escape of fluid 2 or constituents such as solvents or the like—hereinafter also referred to in brief as "fluid evaporation"—depends significantly on the resistance to diffusion through the opened aeration device 28—and therefore, in the first embodiment, depends on the channel 29. On account of its length, the channel 29 produces a relatively large diffusion resistance if it has a sufficiently small hydraulic diameter.

Preferably, the channel 29 has a mean or hydraulic diameter of 0.01 mm to 1 mm. The length of the channel 29 is preferably between 10 times and 1000 times the channel diameter and/or is basically 5 to 50 mm, particularly, preferably, about 10 to 25 mm.

The channel 29 is preferably formed by or on the closure 24. In particular, the channel 29 joins the interior or fluid space 4 of the container 3 to a space 30 in the insertion region of the closure 24 for the delivery element or delivery tube 9, and specifically, preferably, between the sealing element 27 and the cover or seal 25. This connection has the advantage that the aeration device 28 and the channel 29 has no connection with the surroundings when the container 3 is closed—i.e., when the cover or seal 25 is intact—and therefore is likewise closed. Only when the cover and seal 25 are opened, in particular, by piercing or introducing the delivery tube 9, are the connection of the space 30 to the surroundings, and thus the aeration device 28, opened.

In the first embodiment the aeration device 28 is designed for permanent aeration of the fluid space 4 in the container 3 when the closure 24 is opened or pierced for the first time and/or after withdrawal of fluid 2 for the first time. In particular, the aeration device 28 is opened by connecting or introducing the delivery element or delivery tube 9. A piercing element 22, in particular, a separate piercing on the base, is therefore not necessary for the aeration. This simplifies the construction.

The container 3 and the aeration device 28 are preferably opened exclusively by mechanical action or manual actuation. This results in a simple and functionally reliable construction.

With the nebuliser 1 according to the invention, the container 3, the delivery element or delivery tube 9 and/or the associated holder 6 for the container 3 are, preferably, movable in a stroke-like manner during the fluid withdrawal, fluid delivery, pressure generation and/or atomization. The opening and piercing of the container 3 by the delivery tube 9 and the insertion of the delivery tube 9 into the container 3 is preferably produced by this movement and during the initial tensioning of the drive spring 7. Accordingly, in the first embodiment, the opening of the aeration device 28 is preferably produced by the aforementioned movement.

Instead of the aeration device 28 being permanently open, it may also be opened only temporarily, in particular, only during the aforementioned movement. This is also explained in more detail hereinafter with the aid of other preferred embodiments.

The channel 29 preferably runs at least over a section between the cap and insert 26 of the closure 24, on the one hand, and the cover and seal 25, on the other hand. This simplifies manufacture since the channel 29 is formed as an open groove in the insert or cap 26 and can then be covered by the seal 25. In particular, the channel 29 surrounds the delivery tube 9 and/or an insertion opening and/or the space 30 for the delivery tube 9, in an annular or spiral manner, at least over a section 31. Alternatively or in addition, the channel 29 may also run in a meandering or zigzag fashion.

Figure 4:
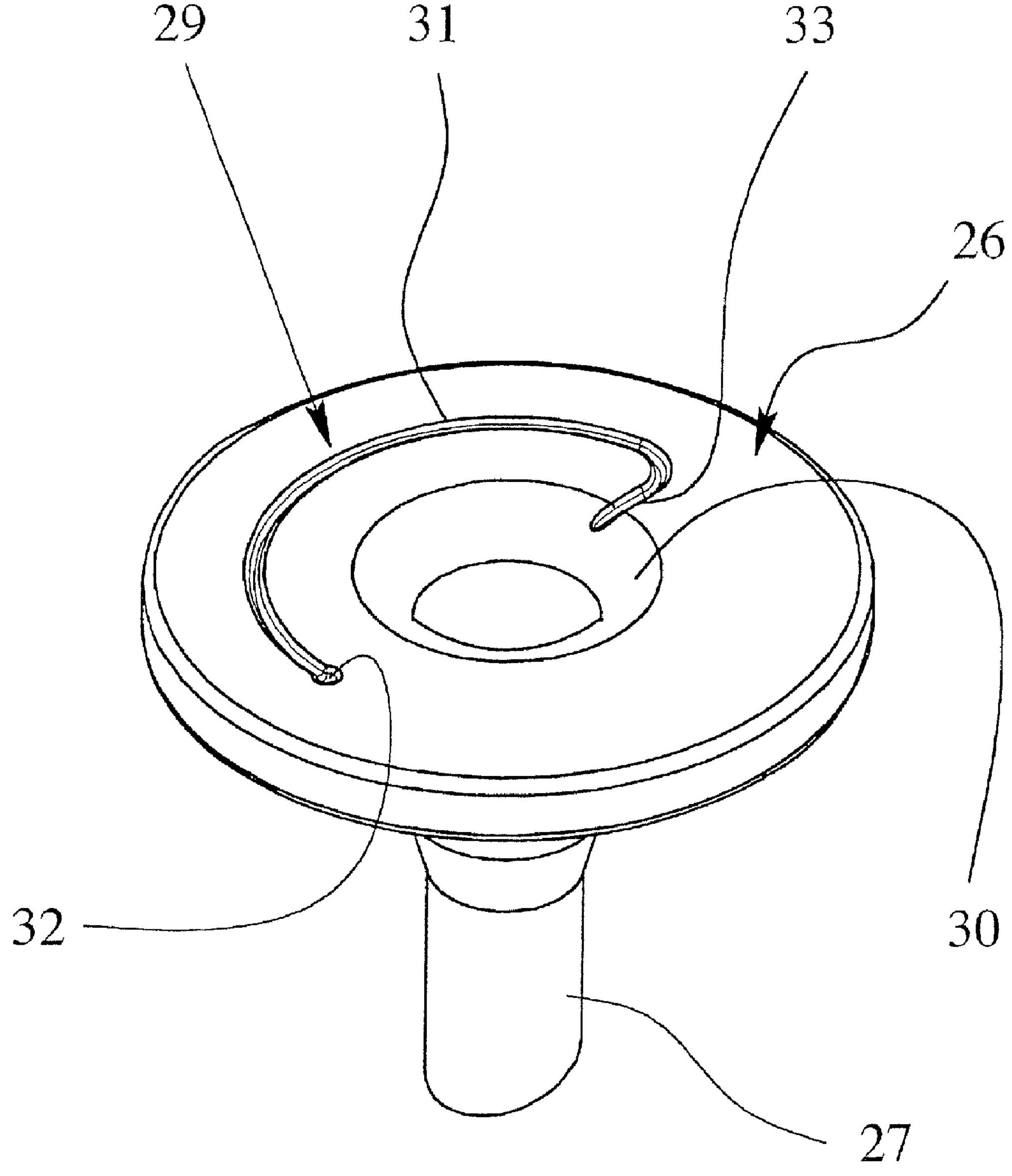
FIG. 4 shows a closure of the container according to FIG. 3.

FIG. 4 illustrates the closure 24 and the insert 26 in a sectional, enlarged representation. In addition to the aforementioned annular section 31, in the first embodiment, the channel 29, preferably, includes an axial section 32 through the insert 26 and an annular flange of the insert 26 for forming a connection to the interior of the container 3. In addition, the channel 29, preferably, comprises a radial section at the other end of the annular section 31 for forming a connection to the space 30, i.e., to the insertion opening and insertion incline or bevel for the delivery tube 9.

When the delivery tube 9 is inserted, a radial gap or annular space exists between the open end of the radial section 33 of the channel 29 and the cylindrical surface of the delivery tube 9, so that the aeration through the channel 29 is not hindered by the delivery tube 9 when the seal 25 is opened. However, the seal 25 may, if necessary, also be configured in such a way—in particular, in the manner of a membrane or the like—and/or may co-operate hermetically with the delivery tube 9, that the free exchange of gas between the space 30 and the surroundings is restricted or prevented, in order to minimize the undesirable vaporization of fluid.

As has already been explained, the aeration device 28 for the direct aeration of the fluid space 4 is formed in the container 3. When the aeration device 28 is open, a direct exchange of gas is possible between the gas space in direct contract with the fluid 2 and the surroundings of the container 3. In order to prevent an escape of fluid 2 through the aeration device 28, the aeration device 28, preferably, comprises at least one semi-permeable element 34 that is impermeable to liquids but permeable to gases. The semi-permeable element 34 thus prevents a possible outflow of the fluid 2 through the aeration device 28.

As is illustrated in FIG. 3, the semi-permeable element 34 is preferably associated with the interior or fluid space 4 of the container 3, i.e., is arranged on the inside or fluid side. In the first embodiment, the channel 29 or its axial section 32, preferably, directly adjoins the semi-permeable element 34, which particularly preferably is arranged directly on or in the closure 24 or its insert 26. The semi-permeable element 34 is, in particular, constructed of a suitable membrane, a non-woven material, a hydrophilic or hydrophobic material or region, or the like, in order to achieve the desired semi-permeability.

The aeration device 28 is configured in such a way as to permit a relatively rapid pressure compensation. This is necessary for example, in the case of rapid successive withdrawal of fluid 2 from the container 3. In particular, the aeration device 28 is configured in such a way that a pressure compensation of at least 20 hPa takes place with a half-life time of at most 60 sec, in particular, 30 sec or less. In the first embodiment this is achieved by suitably dimensioning the channel 29 and the other possible flow resistances, for example, through the semi-permeable element 34.

In the first embodiment, the insert or cap 26 adjoins a dip tube 35, which, for example, is slipped on, and preferably, extends at least substantially as far as the container base 21 in the interior of the container 3. The dip tube 35 is formed, for example, by a flexible silicone tube.

To open the container 3, the delivery tube 9 is inserted into the container 3, whereby the seal 25 is opened and an at least substantially tight connection is formed between the delivery tube 9 and the sealing element 27 of the closure 24. FIGS. 1 & 2 diagrammatically show the state when the delivery tube 9 is inserted into the container 3, and accordingly additional explanation is unnecessary. In the fully inserted state, the delivery tube 9 pierces or opens a seal, for example, at the end or on the base of the sealing element 27, whereby the fluid connection to the interior of the container 3, i.e., to the fluid 2, is formed. The dip tube 35 forms an extension in order to enable the fluid 2 to be withdrawn substantially completely from the container 3 and fluid space 4 in the illustrated, upright position of the container 3.

Further embodiments according to the invention are explained hereinafter with reference to the further figures, though only essential differences compared to the first embodiment and compared to the known implementation of nebuliser 1 and container 3 illustrated in FIGS. 1 & 2 are discussed. The relevant implementations therefore apply as appropriate.

Figure 5:
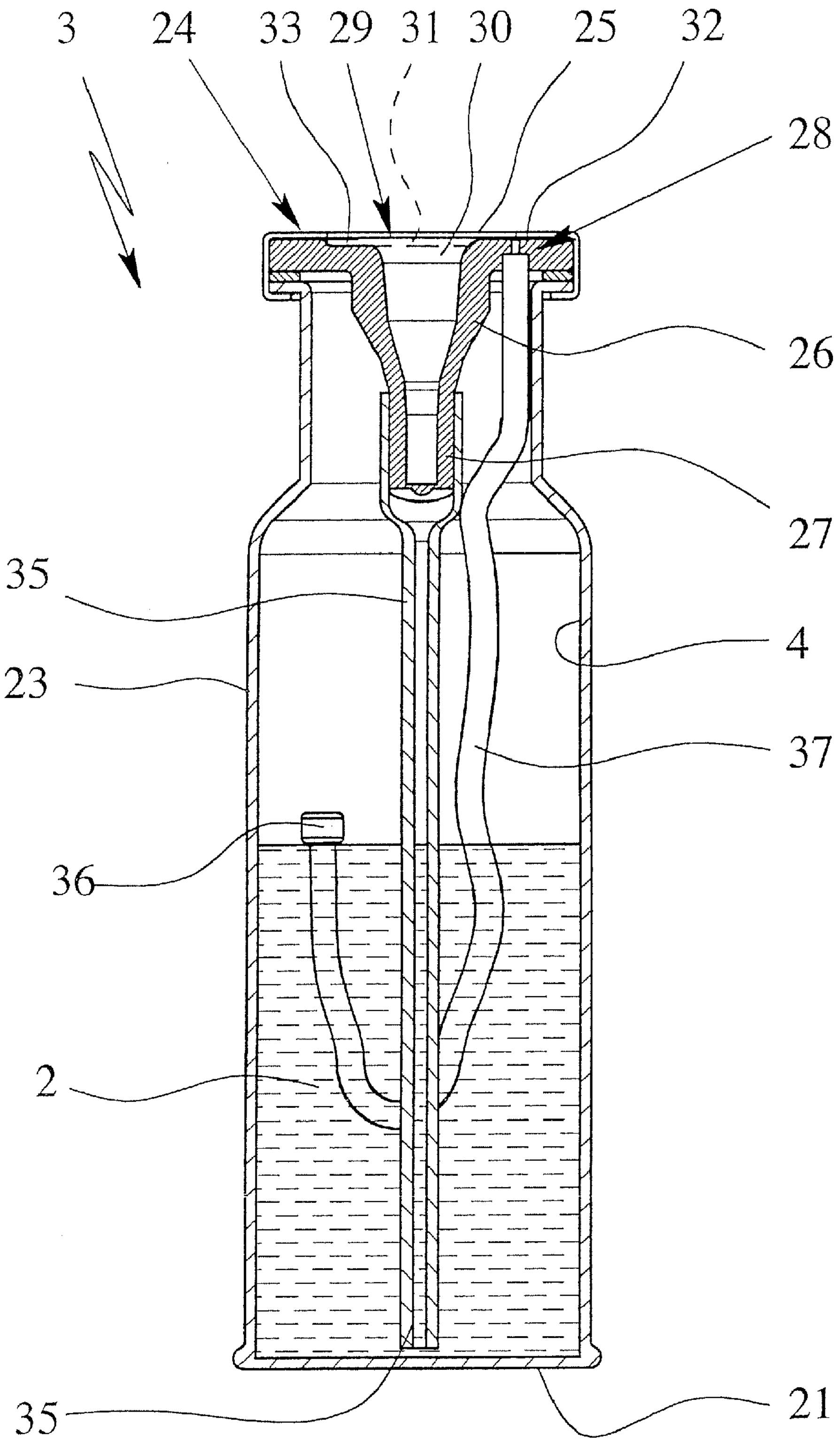
FIG. 5 is a diagrammatic sectional view of a proposed container according to a second embodiment.

FIG. 5 shows, in a diagrammatic sectional view, a second embodiment of the container 3 according to the invention. In contrast to the first embodiment, in this case, the semi-permeable element 34 (not shown) is arranged separately from the closure 24 on or in a float 36 and is connected via a flexible tube 37 to the channel 29, in particular, to the axial section 32 of the said channel 29.

The float 36 always floats on the surface of the fluid 2 in the container 3. Accordingly, the second embodiment permits a de-aeration independently of the position/orientation of the container 3. Furthermore, the use of the float 36 permits a possibly easier, namely position-independent, aeration since, in any arbitrary position of the container 3, no fluid 2 can prevent the direct gas connection between the gas space in the container 3 and the channel 29, with the result that only the pressure of the relevant fluid 2 has to be overcome in the aeration.

Figure 6:
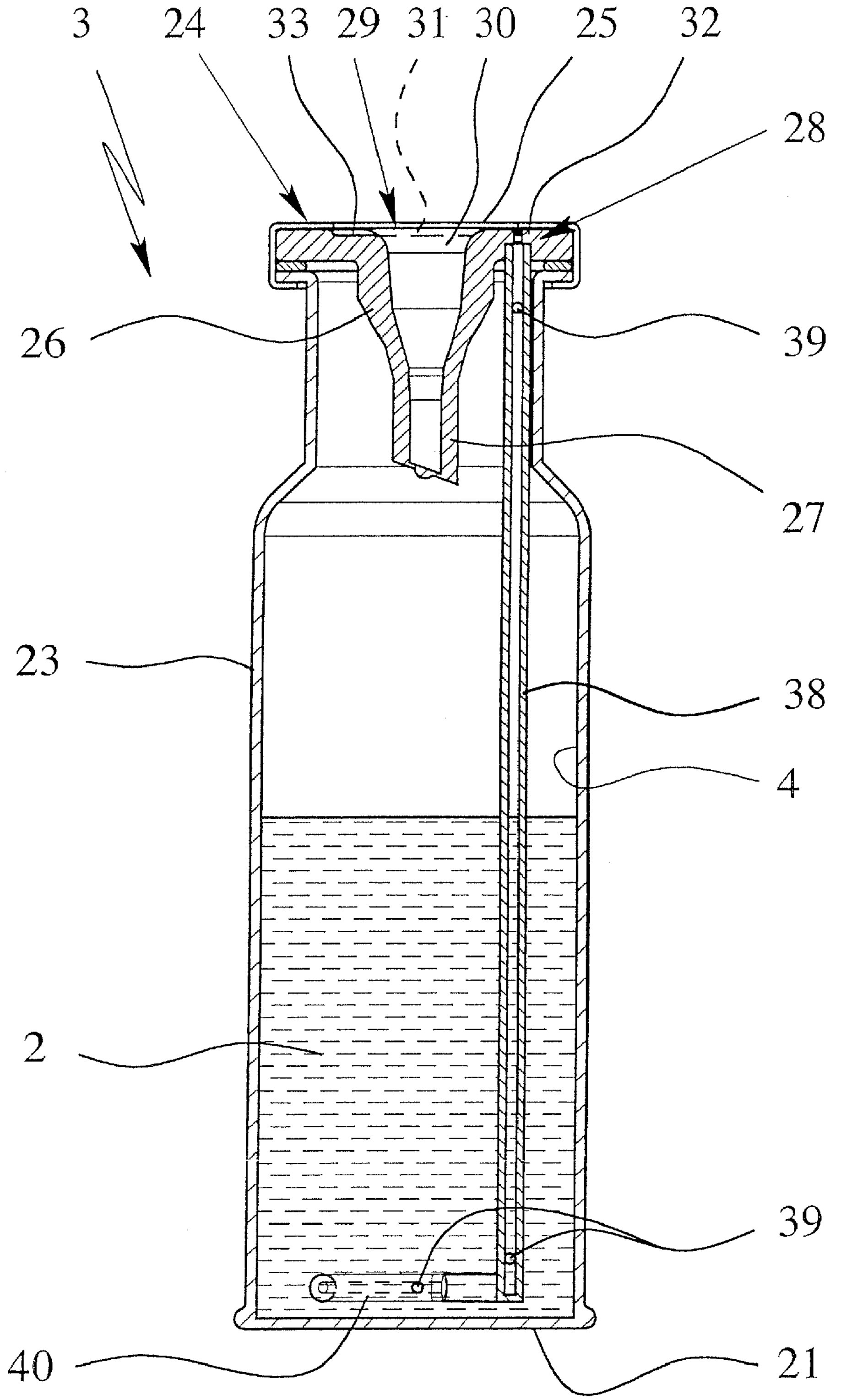
FIG. 6 is a diagrammatic sectional view of a proposed container according to a third embodiment.

FIG. 6 shows a third embodiment of the container 3 according to the invention. Instead of the float 36 and flexible tube 37, in this case, the aeration device 28 comprises a stiff or rigid, preferably tubular aeration element 38. The aeration element 38 extends into the interior of the container 3, in particular, substantially over the whole length of the container 3, and is preferably connected directly to the channel 29 and its axial section 32 and/or to the closure 24 and its insert 26.

The aeration element 38 is preferably formed as a line made of glass or another suitable material. The aeration element 38 comprises at least one, preferably a plurality of aeration openings 39, with each of which is associated a semi-permeable element 34 (not shown), in order, on the one hand, to permit an aeration and/or de-aeration, and on the other hand, to prevent an entry of fluid 2 into the aeration element 38 and an outflow of fluid 2 from the container 3 through the aeration device 28. Alternatively or in addition, the semi-permeable element 34 or material may also be arranged in the aeration element 38.

Preferably, the aeration openings 39 are provided in the region of the head and its closure 24 of the container 3, as well as in the region of the container base 21. In addition, a plurality of aeration openings 39 are preferably formed in the region of the container base 21 on a lateral section 40 of the aeration element 38 extending at least substantially in a radial plane. A very good aeration and/or de-aeration is thereby effected, independently of the position of the container 3.

Figure 7:
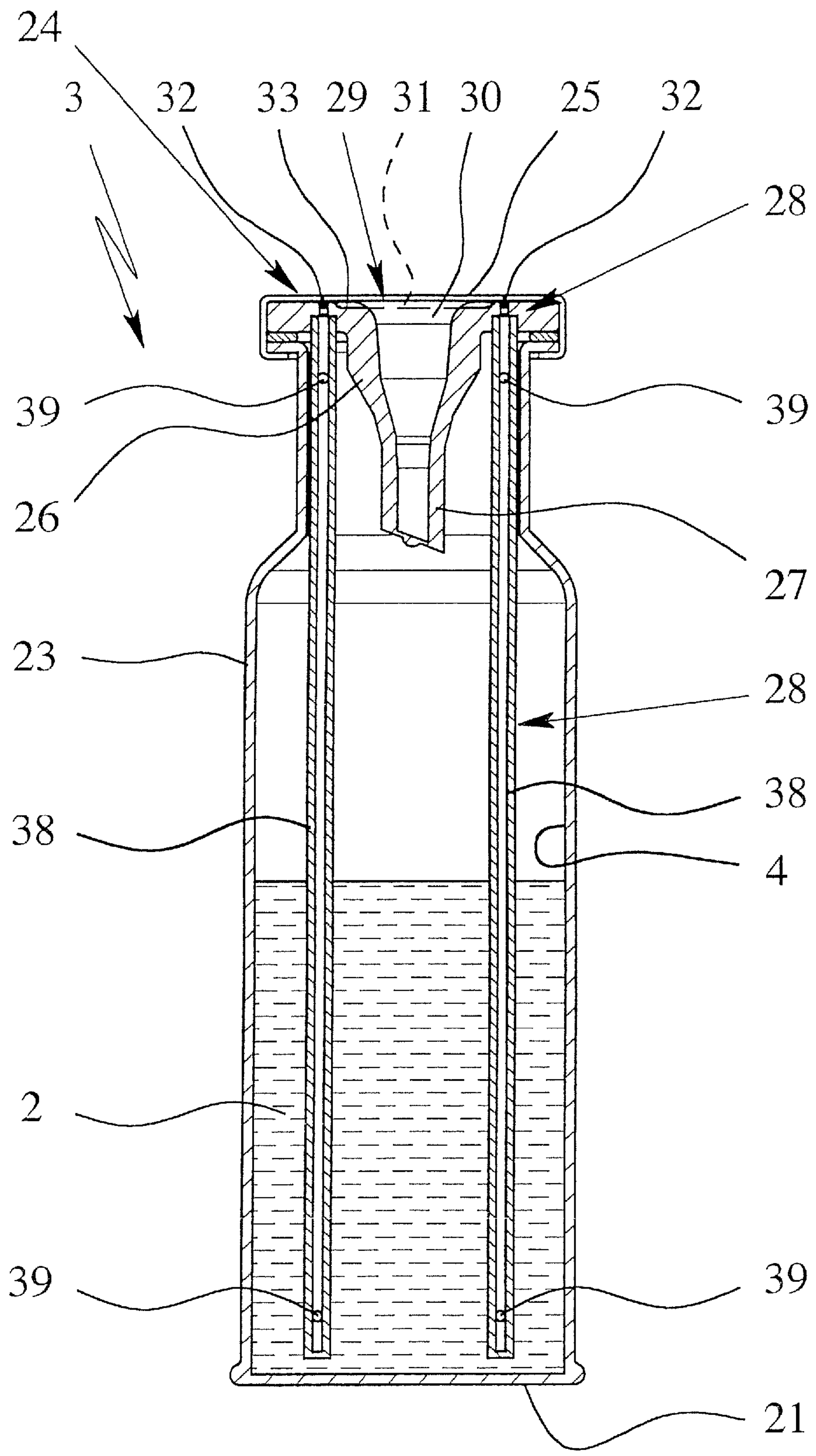
FIG. 7 is a diagrammatic sectional view of a proposed container according to a fourth embodiment.
Figure 8:
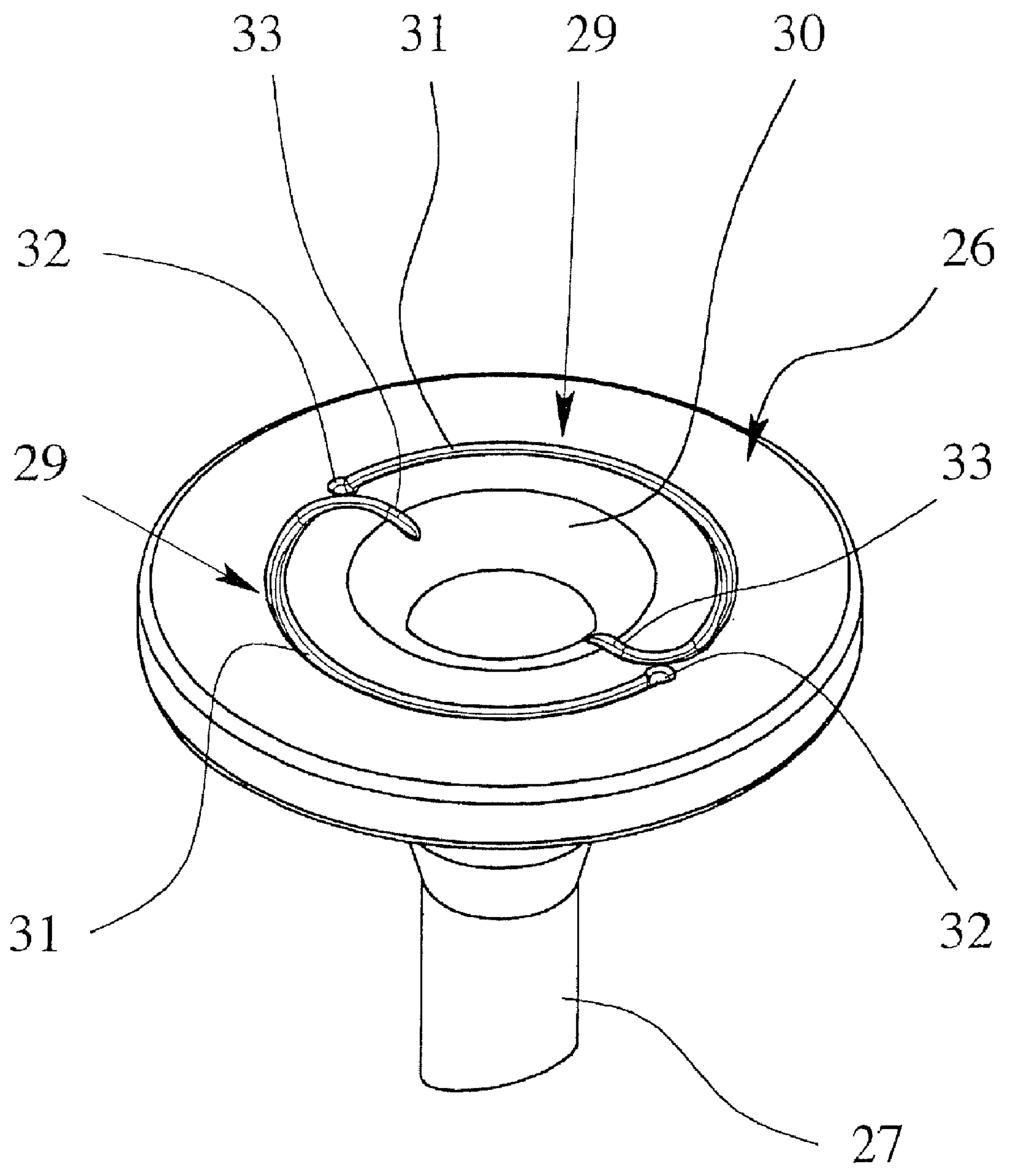
FIG. 8 shows a closure of the container according to FIG. 7.

FIG. 7 shows a diagrammatic section of the container 3 according to the invention and in accordance with a fourth embodiment. Compared to the previous embodiments, the aeration device 28 comprises two separate, independent channels 29 for aeration, as illustrated in the enlarged representation of the insert 26 according to FIG. 8. Corresponding to the third embodiment, an aeration element 38 adjoins each channel 29 preferably formed corresponding to the previous embodiments, though no transverse sections 40 are provided. The aeration openings 39 of the aeration elements 38 are, in turn, preferably, covered and closed by semi-permeable elements 34, the semi-permeable elements 34, as in FIG. 6, likewise not being shown for the sake of simplicity.

A particular advantage of the fourth embodiment is that, with a plurality of parallel channels 29, a possible blockage of one channel 29 does not lead to a failure of the aeration. A particularly high functional reliability is thus ensured. Apart from this, the previous explanations, in particular, as regards the third embodiment, apply correspondingly to the fourth embodiment.

Figure 9:
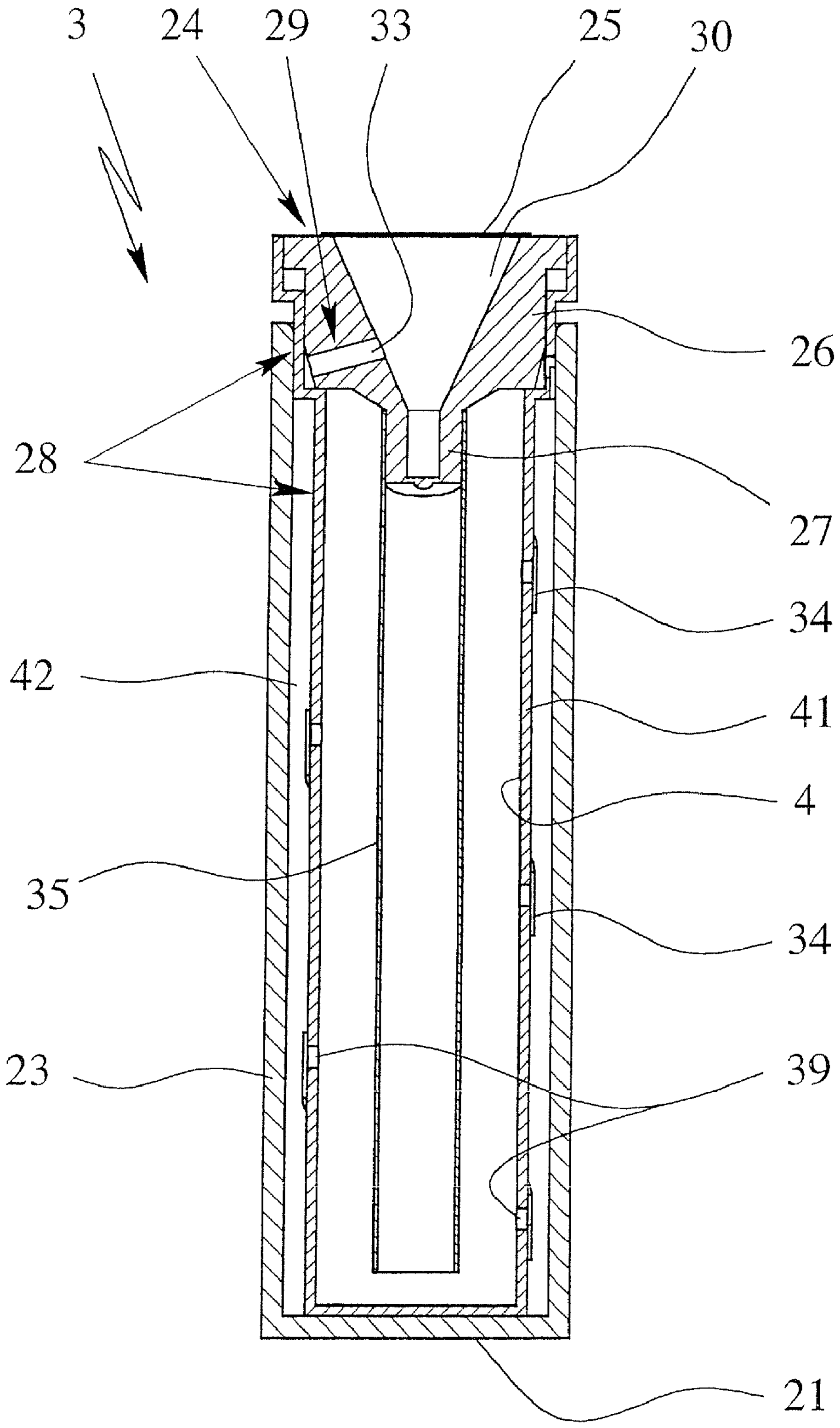
FIG. 9 is a diagrammatic sectional view of a proposed container according to a fifth embodiment.

FIG. 9 shows, in a diagrammatic sectional view, a fifth embodiment of the container 3 according to the invention. The container 3 comprises, in this embodiment, an inner container 41 for holding the fluid 2 that is made, in particular, of plastics, for example, polypropylene. In the illustrated example, the inner container 41 is formed separately from the closure 24. Preferably, the inner container 41, together with the closure 24 and its insert 26, are incorporated into the outer case 23, the inner container 41 together with the closure 24 and its insert 26 preferably being assembled, combined or joined in some other way so as to form a leak proof container space for the fluid 2. Preferably, the inner container 41 is secured together with the closure 24 or by means of the closure 24 in the container 3.

In the fifth embodiment, the channel 29 basically comprises only a radial section 33, as indicated in FIG. 9. This section joins the space 30 to an intermediate space 42 that is formed between the inner container 41 and the outer case 23 and has, in particular, an annular configuration.

The inner container 41 is designed having at least one aeration opening 39, preferably a plurality of aeration openings 39, to the intermediate space 42 which, in turn, are covered or closed by associated semi-permeable elements 34, as indicated in FIG. 9. If necessary, the aeration openings 39 may also be formed by slits or the like. Preferably, the aeration opening 39 also extends helically or spirally or in the manner of a screw around the cylindrical surface of the inner container 41, which is preferably designed at least substantially oblong and cylindrical corresponding to the container 3. The associated semipermeable element 34 is then preferably formed as a continuous cover strip or the like and is arranged in particular, on the outside of the inner container 41. A particularly good aeration and de-aeration can thus be achieved in any position of the container.

In the fifth embodiment, the dip tube 35 is preferably formed by a flexible silicone tube or the like which, in particular, is attached to the insert 26 or its sealing element 27 or is connected thereto in some other way.

Alternatively or in addition to the channel 29, the aeration device 28 may, in all embodiments, include a valve (not shown) for opening and closing the aeration device 28. In particular, the valve, and thus the aeration device 28, is opened only temporarily, and therefore, in contrast to the previously-described embodiments, not permanently when the container 3 is open.

If necessary, the valve may be opened only when a certain pressure difference is exceeded and/or only temporarily during the aforementioned movement, i.e., in particular, during the stroke-like movement involved in fluid withdrawal, fluid delivery, pressure generation and/or atomization of the container 3, delivery element 9 and/or associated holder 6.

The valve (not shown) is preferably integrated into the closure 24. Alternatively or in addition, the valve may, however also be arranged separately from the closure 24 on the container 3, for example, on the base or at the side on the cylindrical surface, or separately from the container 3 on the nebuliser 1.

According to a further variant (not shown), the aeration device 28 may also be formed by an automatically closing membrane, an automatically closing septum, or the like. In this case too, the aeration device 28 may again, if necessary, be arranged on or in the closure 24 or separately therefrom, in particular, on the base or on the circumstantial surface of the container 3.

According to a further variant (not shown), the aeration device 28 may also comprise an, in particular, radial, preferably closable, aeration opening 39 arranged on the outer case 23 of the container 3, for aerating and de-aerating the fluid space 4 of the container 3.

Figure 10:
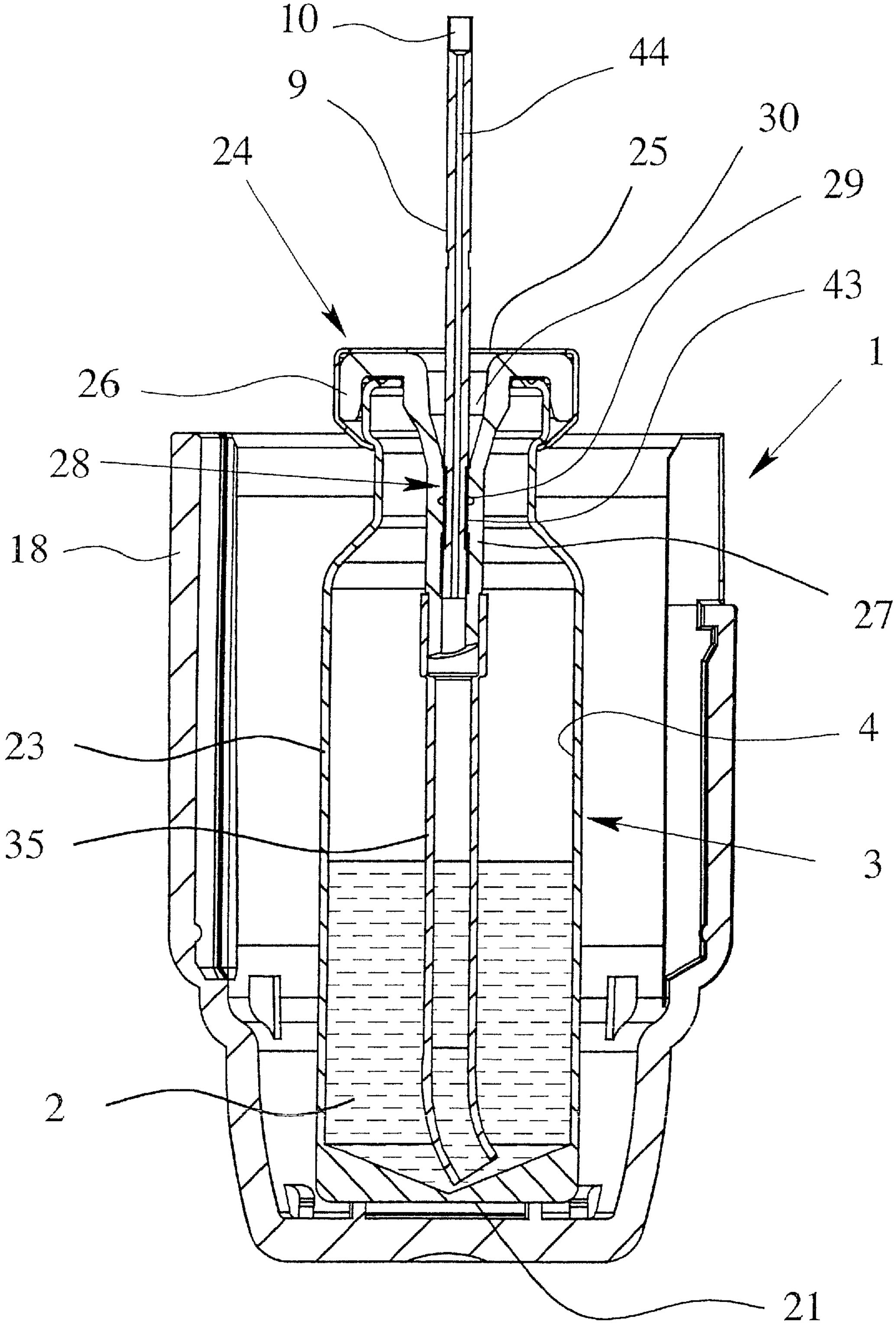
FIG. 10 is a diagrammatic sectional view of a proposed container and of parts of the proposed nebuliser according to a sixth embodiment.

FIG. 10 shows, in a diagrammatic sectional view, the container 3 according to the invention and a part of the associated nebuliser 1 according to the invention and in accordance with a sixth embodiment.

In the previous embodiments, the aeration device 28 was arranged and formed exclusively on the container 3. In the sixth embodiment, the aeration device 28 is arranged or formed at least partly or completely on the nebuliser 1, and in particular, therefore, not on the container 3.

The aeration device 28 in the sixth embodiment includes a bypass on the delivery element or delivery tube 9, which is formed on the outside, in particular, by a preferably oblong or screw-shaped flute 43, groove, flat section or the like. Thus, the bypass also runs axially, in order to form, in particular, a connection between the insertion region or space 30 of the closure 24 and the interior of the container 3 when the aeration device 28 is open. To this end, the channel 29 is also provided in the region of the sealing element 27, which preferably runs radially and forms the connection between the bypass within the sealing element 27 and the interior of the container 3.

Preferably, the bypass—in particular, as regards its axial position and length—and the axial arrangement of the channel 29 as well as the axial position and length of the sealing element 27 are matched to one another in such a way that, with a relative movement of the delivery tube 9 towards the container 3 and the sealing element 27, the aeration device 28, i.e., the gas connection between the interior of the container 3 and the surroundings, is only temporarily opened. In the sixth embodiment, the delivery tube 9 is, for this purpose, axially moveable or displaceable relative to the container 3 during the tensioning of the nebuliser 1 for the withdrawal of fluid and during the release of the tensioning, i.e., during the pressure generation and atomization of the fluid 2. In this connection, the container 3 can, for example, be held rigidly, i.e., not axially displaceably, in the housing part 18. However, it is conversely also possible for the delivery tube 9 to be fixed in the nebuliser 1 and for the container 3 to move preferably in a stroke-like manner during the tensioning and detensioning procedure.

On account of the aforementioned preferred relative movement of the delivery tube 9 in the container 3, the delivery tube 9 adopts, relative to the sealing element, two different end positions in the primed nebuliser 1—i.e., after withdrawal of fluid—and in the deprimed nebuliser 1—i.e. after the atomization stroke. Preferably, in the sixth embodiment, a closure of the aeration device 28 takes place in at least one of the two end positions, preferably in both end positions. In the illustrated example, this is achieved by virtue of the fact that, in the two end positions, a section of the delivery tube 9, arranged as desired either axially above or below the bypass, co-operates with the sealing element 27—in particular, with the part of the sealing element 27 arranged axially above the channel 29 in FIG. 10—in such a way, a sealing of the connection between the channel 29 and the space 30 in the two aforementioned end positions of the delivery tube 9 takes place. In the sixth embodiment, the aeration device 28 is, therefore, preferably, open only during the tensioning and release of tensioning movements, i.e., is open only temporarily. This minimizes evaporation of fluid.

Figure 11:
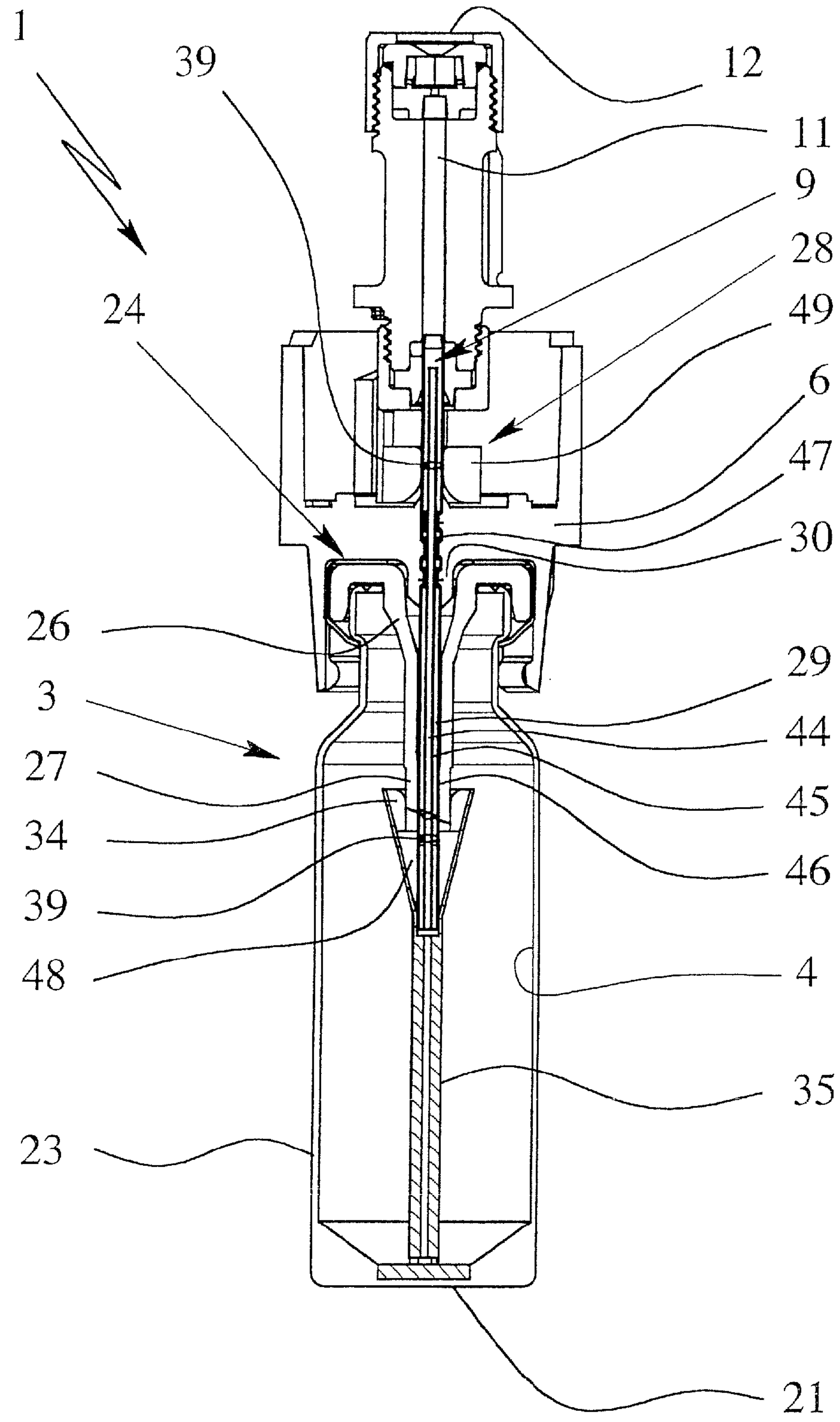
FIG. 11 is a diagrammatic sectional view of a proposed container and of parts of the proposed nebuliser according to a seventh embodiment.

During the tensioning procedure for the withdrawal of fluid, the part of the delivery tube 9 arranged axially underneath the bypass and the part of the sealing element 27 arranged axially underneath the channel 29, as shown in FIG. 11, act hermetically in such a way that fluid 2 can be sucked via the dip tube 35 from the container 3 through the delivery channel 44 formed in the delivery tube 9, and can thereby be withdrawn from the container 3.

According to a variant (not shown), the semi-permeable element 34 or corresponding semi-permeable material is arranged in the bypass, i.e., in particular, the flute 43, groove, flat section or the like is filled therewith so that only the passage of gas is permitted, but an outflow of fluid 2 through the bypass is prevented.

In the sixth embodiment, the bypass is arranged on the outside on the delivery tube 9. However, in principle, the bypass may be arranged on another part or at another site. In particular, the bypass may also be arranged internally in the delivery tube 9. This is discussed hereinafter with the aid of the seventh embodiment and further embodiments.

FIG. 11 is a diagrammatic sectional view a seventh embodiment of the container 3 according to the invention and a part of the associated nebuliser 1 according to the invention. The bypass is, in this case, formed in the delivery tube 9 by the channel 29 for aeration and de-aeration, which runs in particular, axially and preferably parallel to the delivery channel 44. In principle, the delivery channel 44 and the channel 29 may run in parallel to one another in the delivery tube 9 or in another delivery element. Preferably, the channel 29 and the delivery channel 44 are, however, arranged concentrically with respect to one another, and in particular, the channel 29 surrounds the delivery channel 44, at least over an axial length necessary for the formation of the bypass.

Particularly preferably, the delivery tube 9 comprises an inner tube 45 and an outer tube 46, which are arranged concentrically with respect to one another. The inner tube 45 forms the delivery channel 44 in the interior. The annular space between the inner tube 45 and the outer tube 46 forms the aeration channel 29.

The two tubes 45, 46 are securely joined to one another, preferably by welding, for example, in the region of their ends. However the two tubes 45, 46 may also be joined to one another in another suitable way, for example, by adhesion, soldering, deforming or the like.

The multipart design of the delivery tube 9—either from the two tubes 45, 46, as explained hereinbefore, or from even more parts—may, if necessary, also be employed independently of the aeration and aeration device 28, in particular, in a nebuliser 1 of the type mentioned in the introduction or in another nebuliser 1. In particular, in this connection, the aeration channel 29 in the delivery tube 9 may be omitted or sealed. The multipart design allows, in particular, an inexpensive and/or dimensionally accurate production of the delivery tube 9.

In the seventh embodiment, the delivery tube 9 is securely joined to the holder 6. In particular, the delivery tube 9 or its outer tube 46 is, for this purpose, provided with a holding region 47 having a corrugated outer contour or the like. The delivery tube 9 is injection molded together with the holding region 47 into the holder 6. Thus, the holder 6, preferably, engages the holding region 47 in a positive interlocking manner. The delivery tube 9 is thus axially fixed in the holder 6 in a positive interlocking manner.

The delivery tube 9, in the illustrated example, preferably, comprises radial aeration openings 39 in the outer tube 46, in order to produce a gas connection to the channel 29. Preferably, at least one inner aeration opening 39 (in the diagram according to FIG. 11 lying axially underneath, in the region of the container 3) and at least one outer aeration opening 39 (in the diagram according to FIG. 11 lying axially above, outside the sealing element 27 and closure 24) are provided. Instead of the inner and/or outer aeration opening 39, the outer tube 46 may also terminate in the corresponding region in order to permit a gas connection to the channel 29.

The inner aeration opening 39 is situated in an aeration region 48 that is arranged, with respect to the sealing element 27, axially within the container 3 and is formed by the closure 24 and its insert 26 or by the adjoining dip tube 35, in particular, by means of a V-shaped or funnel-shaped widening or the like. The aeration region 48 is in contact with the interior of the container 3 in particular, with a gas space above the fluid 2 (not shown in FIG. 11) in the container 3.

In order to prevent fluid 2 penetrating into the aeration region 48 and through the inner aeration opening 39 into the channel 29, the aeration space 48 is preferably sealed by the semi-permeable element 34 with respect to the interior of the container 3 and thus against the fluid 2. In the illustrated example, at least one semi-permeable element 34 is arranged between the insert 26 and the dip tube 35. Furthermore, the delivery tube 9 with its free end, optionally, only with its inner tube 45 projecting axially relative to the outer tube 46, seals the aeration region 48 by bearing against or engagement in the dip tube 35. However, other structural solutions are also possible in this case.

Alternatively or in addition, the semi-permeable element 34 or material may also be arranged directly in the delivery tube 9 or channel 29.

In particular, however, the arrangement of the inner aeration opening 39 underneath the sealing element 27 is not absolutely necessary. For example, this arrangement may also be provided in the region of the space 30 or in the region of sealing element 27, as in the sixth embodiment.

From what has been said hereinbefore, it follows that, in the seventh embodiment, in contrast to the sixth embodiment, the delivery tube 9 is not moved relative to the container 3 or closure 24 for withdrawal of fluid, in particular, during the tensioning and untensioning of the nebuliser 1.

Depending on the dimensioning of the channel 29 formed in the delivery tube 9 and the relevant requirements, the aeration device 28 according to the seventh embodiment may, after the piercing and opening of the container 3, i.e., after insertion of the delivery tube 9, remain permanently open or may be opened only temporarily, in particular, only during the withdrawal of fluid or if a certain pressure difference is exceeded.

A seal 49 of the aeration device 28, which is associated with the outer end of the channel 29 and with the outer (surrounding atmosphere side) aeration opening 39 of the channel 29, is shown very diagrammatically in FIG. 11. The seal 49 permits the aforementioned, temporary closure of the channel 29, i.e., closure of the aeration device 28, in particular, by a temporary radial covering of the aeration opening 39 or of a plurality of aeration openings 39, possibly superimposed on one another.

Various structural solutions are possible for the opening and closure of the aeration device 28, i.e., for the temporary closure, in particular, of the outer aeration opening(s) 39. Individual structural solutions are explained hereinafter with the aid of further embodiments and with reference to FIGS. 12 to 23.

Figure 12:
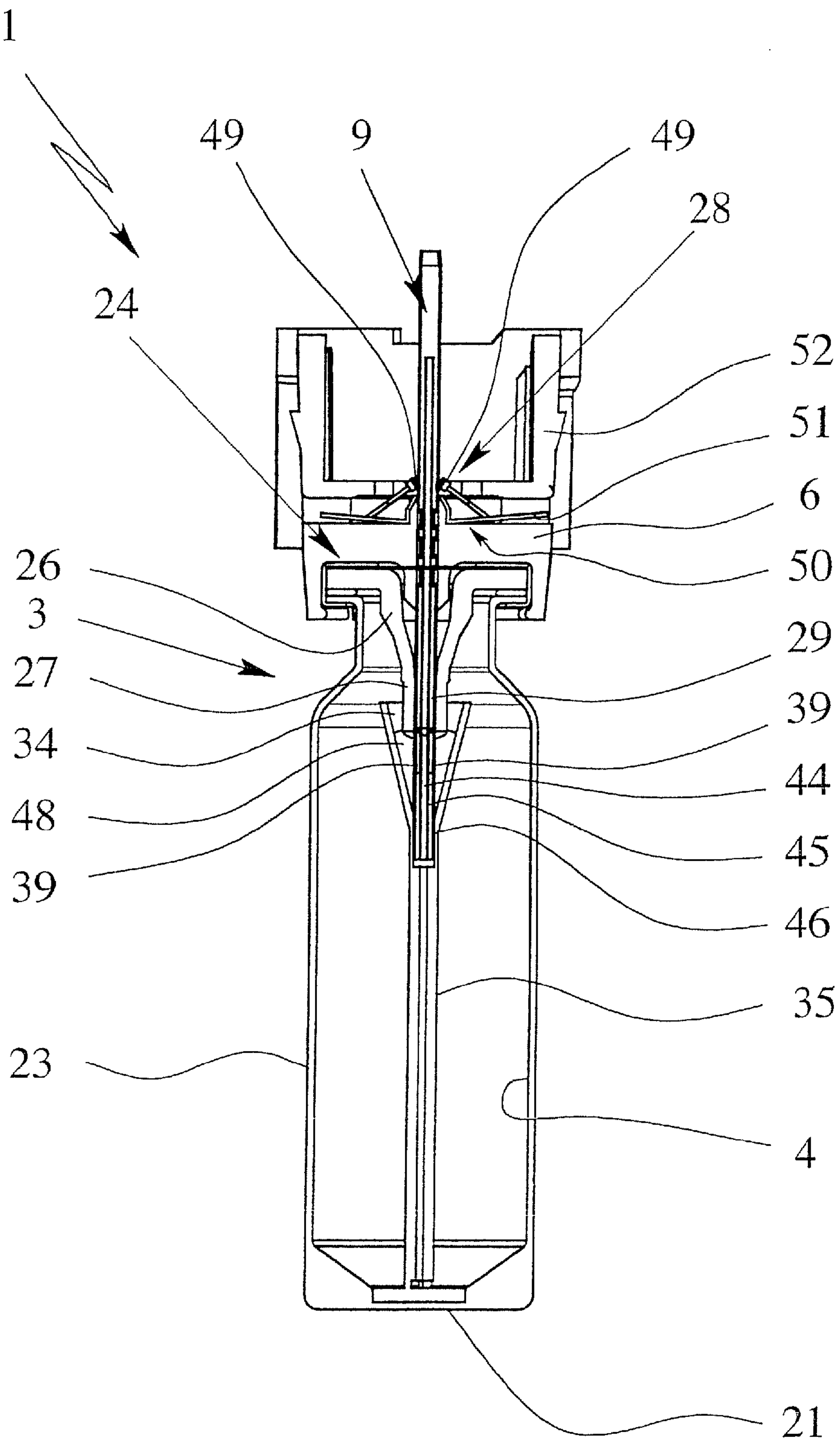
FIG. 12 is a diagrammatic sectional view of a proposed container and of parts of the proposed nebuliser according to an eighth embodiment.
Figure 13:
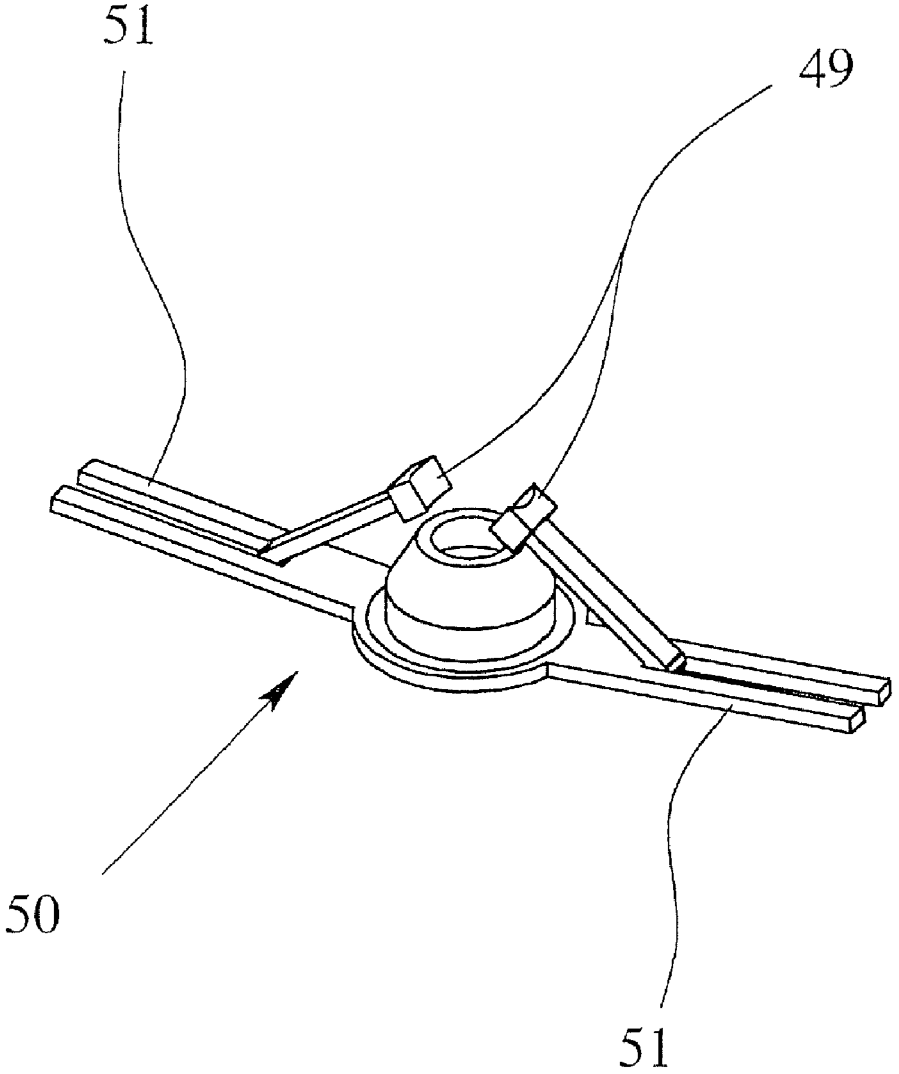
FIG. 13 is a diagrammatic sectional view of a part of the nebuliser according to FIG. 12.

FIG. 12 is a diagrammatic sectional view of an eighth embodiment of the nebuliser 1 (only in part) according to the invention and of the container 3. Seals 49 are, in this case, forced resiliently by a spring element 50, shown on an enlarged scale in FIG. 13, onto oppositely lying, outer (nebuliser-side) aeration openings 39. The spring element 50 preferably comprises radial actuating arms 51, which during the tensioning procedure—i.e., during the stroke movement of the holder 6 and of the container 3 downwardly for the tensioning of the drive spring 7 and for the fluid removal—are deflected or actuated by an actuating part 52 in the nebuliser 1 against the spring force in such a way that the seals 49 free the outer aeration openings 39. In the tensioned state, i.e., in the lower end position of the container 3, the actuating arms 51 can them raise the actuating part 52 again, so that the spring element 50 closes the outer aeration openings 39 again on account of its spring force. In the twelfth embodiment, only a temporary opening of the aeration device 28 therefore takes place, exclusively during the removal of fluid and the tensioning stroke.

Figure 14:
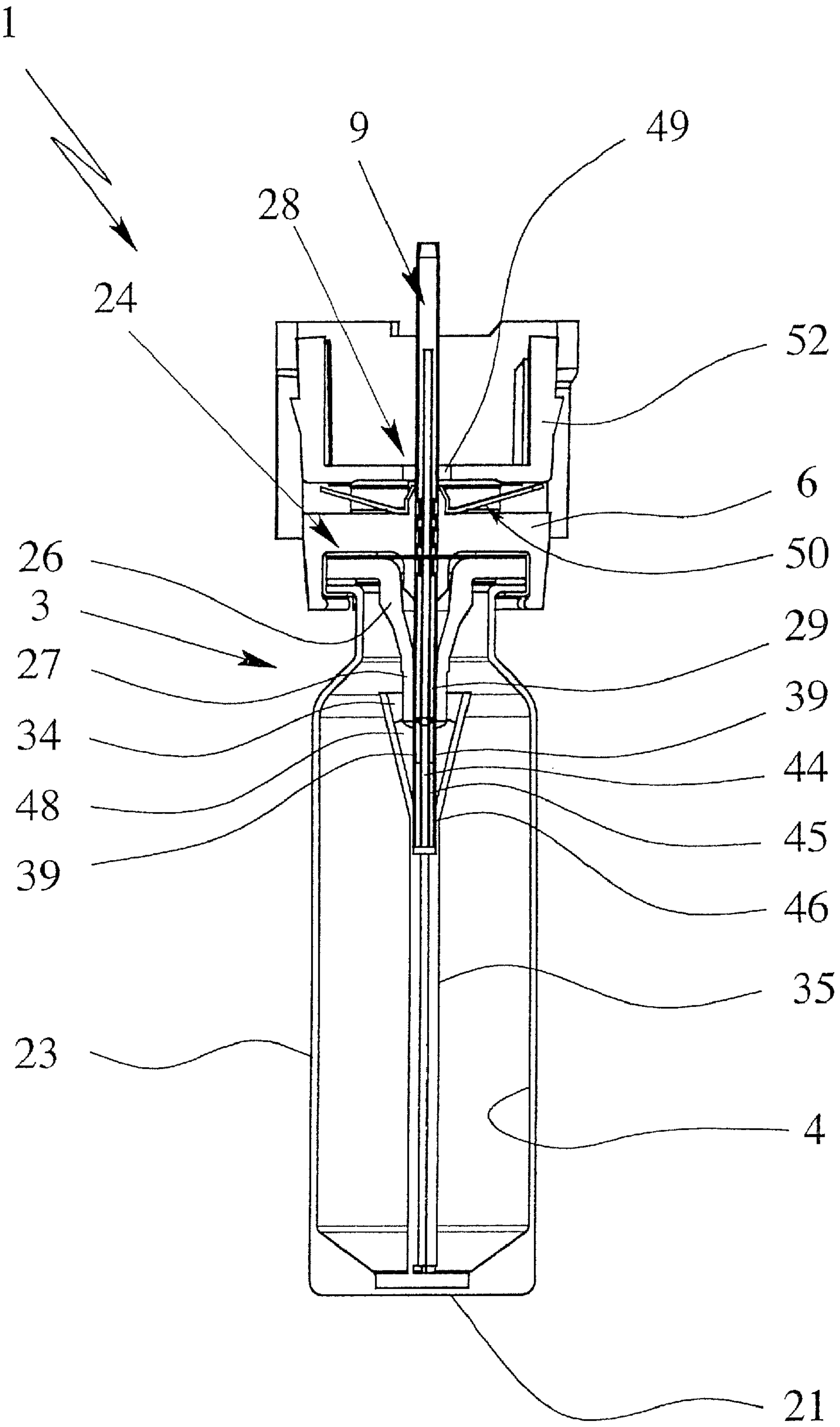
FIG. 14 is a diagrammatic sectional view of a proposed container and of parts of the proposed nebuliser according to a ninth embodiment.
Figure 15:
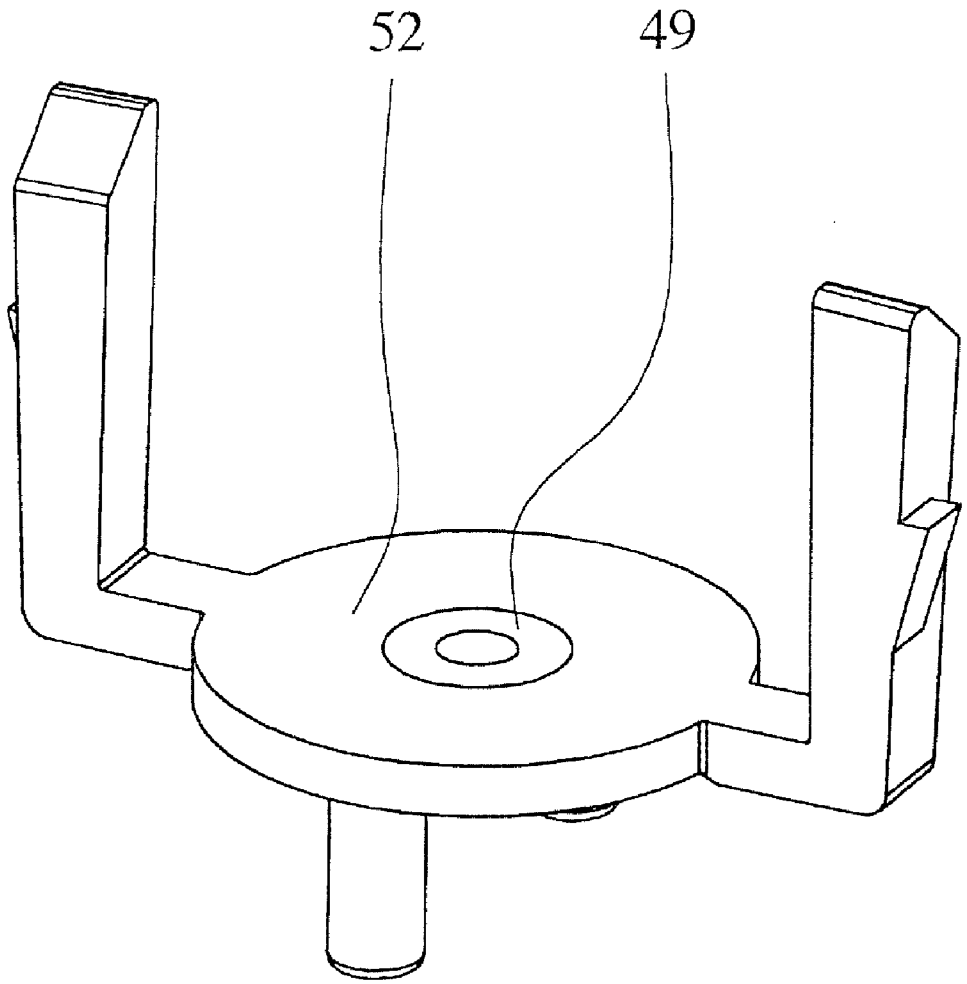
FIG. 15 is an enlarged diagrammatic sectional view of a part of the nebuliser according to FIG. 14.

FIG. 14 is a diagrammatic sectional view of a ninth embodiment of the nebuliser 1 (only in part) according to the invention and of the container 3. Again, preferably two outer, oppositely facing aeration openings 39 are provided on the nebuliser side, corresponding to the eighth embodiment. In contrast to the eighth embodiment, the actuating part 52 comprises an annular seal 49 surrounding the delivery tube 9 and covering the aeration openings 39 in the closed state. FIG. 15 shows the actuating part 52 with the annular seal 49 in a separate, enlarged representation.

The actuating element 52 is held in a resilient manner by the associated spring element 50 in the position covering the aeration openings 39. When the nebuliser 1 is primed, the actuating element 52 is displaced axially against the spring force of the spring element 50, whereby the aeration openings 39 are at least temporarily freed and opened. In the rest state—also in the primed state—the aeration openings 39 are closed again on account of the restoring force of the spring element 50. In the ninth embodiment, preferably, corresponding to the eighth embodiment, there takes place simply a temporary opening of the aeration device 28, exclusively during the tensioning procedure and during the withdrawal of fluid.

Figure 16:
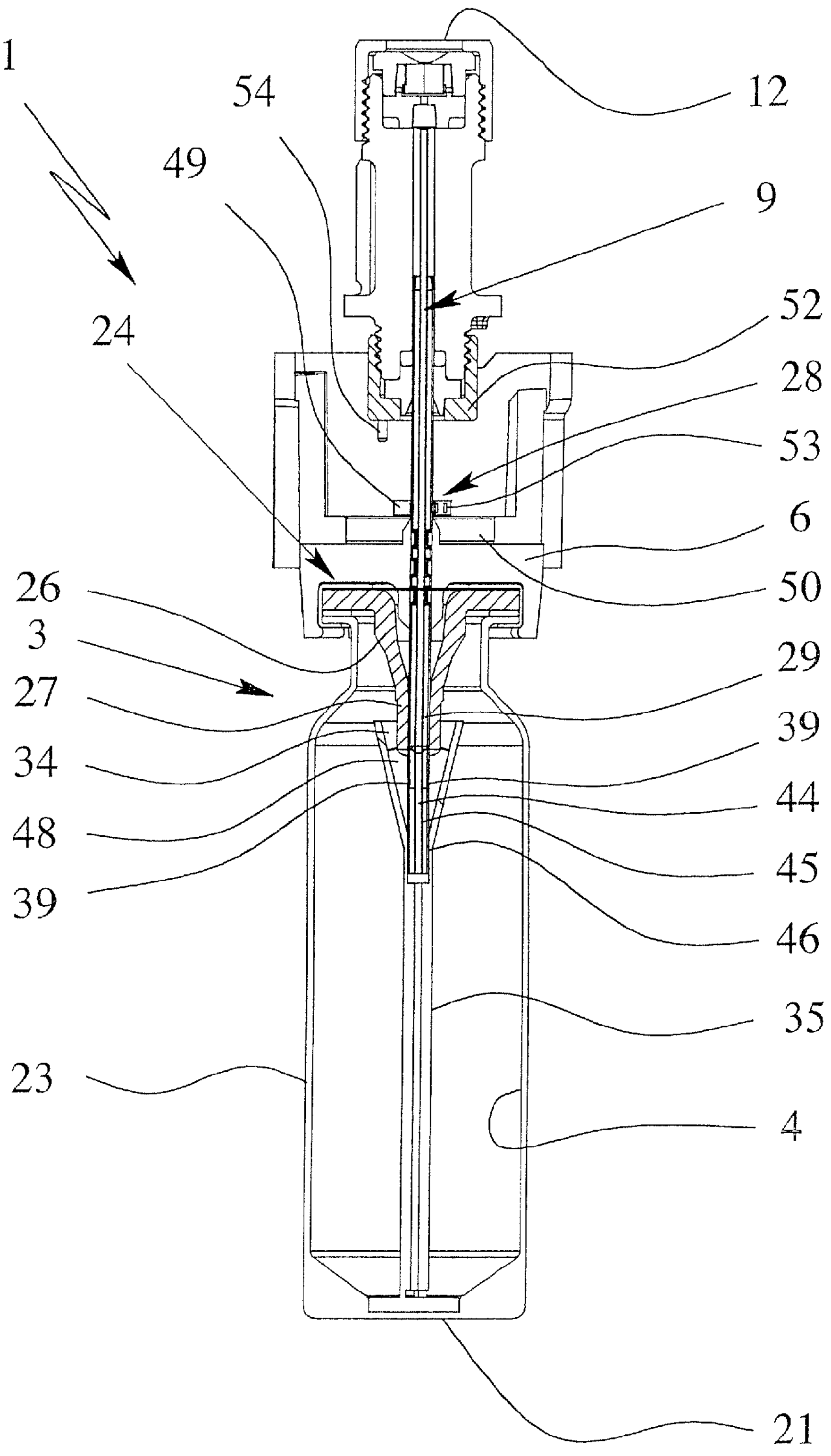
FIG. 16 is a diagrammatic sectional view of a proposed container and of parts of the proposed nebuliser according to a tenth embodiment.
Figure 17:
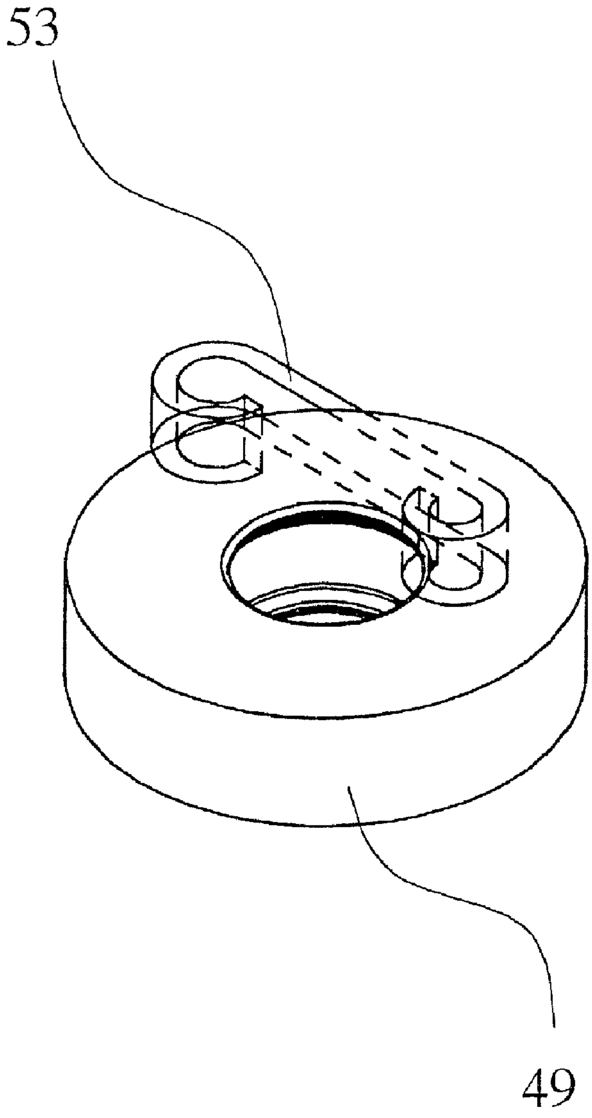
FIG. 17 is a diagrammatic sectional view of a part of the nebuliser according to FIG. 16.

FIG. 16 is a diagrammatic sectional view of a tenth embodiment of the nebuliser 1 according to the invention (only in part) and of the container 3. In the tenth embodiment, the aeration device 28 preferably comprises an at least substantially annular seal 49 that covers and seals the outer aeration openings 39 in the closed state. However, in contrast to the ninth embodiment, the seal 49 is preferably securely attached to the delivery tube 9 and is provided with a lever 53 or the like, as is illustrated in the representation of the seal 49 according to FIG. 17. A rotational movement (rotation of the housing part 18) takes place when the nebuliser 1 is primed, which movement is used to swivel the lever 53 in the radial plane and thereby deform the seal 49 in such a way that the aeration opening(s) is/are freed. The actuation is preferably effected by means of a projection 54 on an actuating part 52 or the like of the nebuliser 1. After actuation, a closure and sealing of the aeration opening(s) 39 again takes place through the seal 49 on account of its elasticity and restoring forces. Thus, in the tenth embodiment, preferably, only a temporary opening of the aeration device 28 takes place, in particular, only during the withdrawal of fluid from the container 3.

Figure 18:
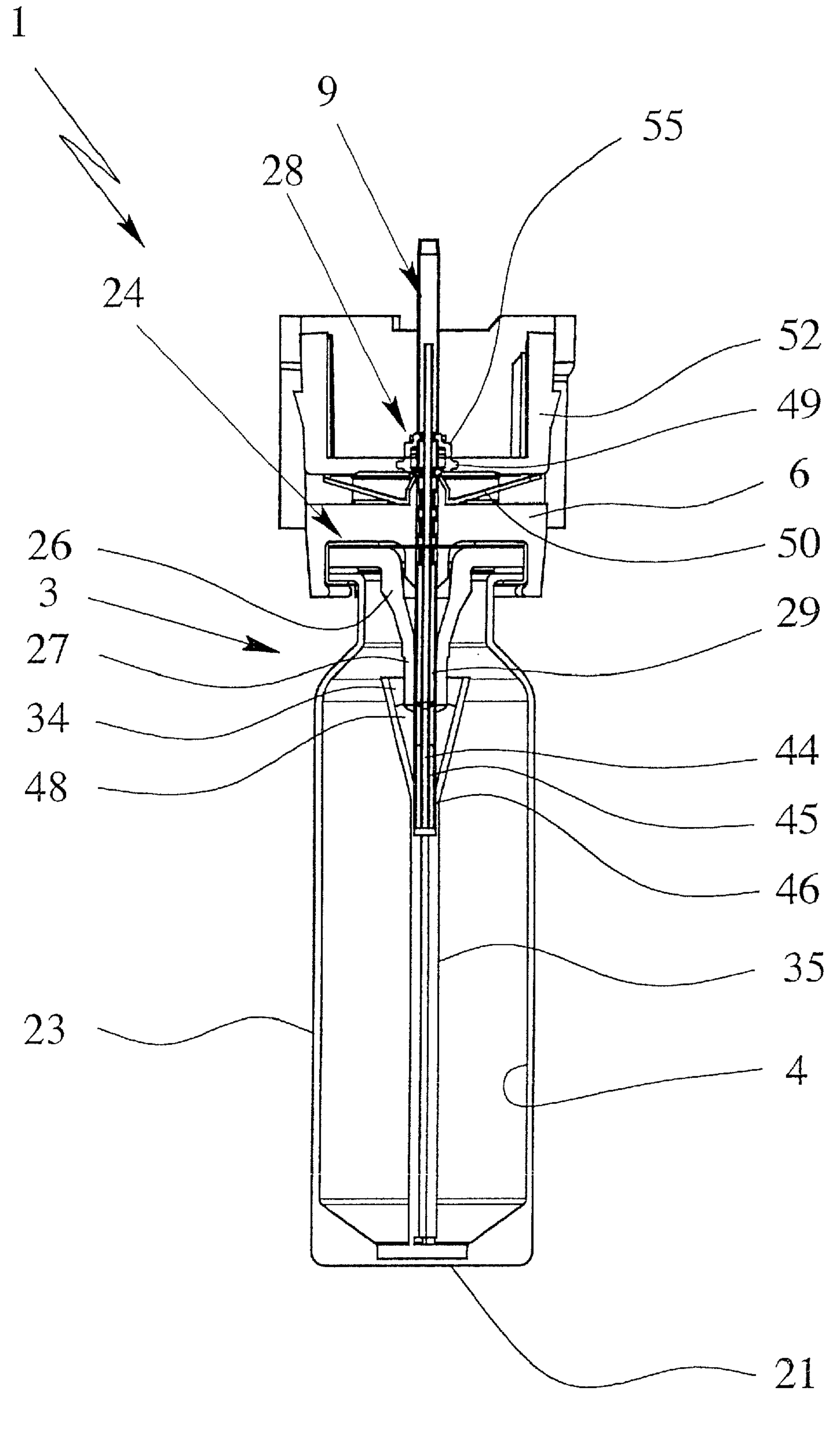
FIG. 18 is a diagrammatic sectional view of a proposed container and of parts of the proposed nebuliser according to an eleventh embodiment.

FIG. 18 shows, in a diagrammatic sectional view, an eleventh embodiment of the nebuliser 1 according to the invention (only in part) and of the container 3. The eleventh embodiment is fairly similar to the ninth embodiment. However, in contrast to the ninth embodiment, in the eleventh embodiment, the seal 49 does not directly seal off the aeration openings 39, but instead co-operates with a counter-seal 55 that is securely arranged on the delivery tube 9.

In the illustrated closed state the actuating part 52 is axially pretensioned by the associated spring element 50 with respect to the counter-seal 55, so that the seal 49 is pressed axially tightly against the counter-seal 55. A closed sealing space is thus formed around the aeration opening(s) 39. The seal 49 may optionally comprise an annular, elastic flange or the like to provide a bearing surface for or connection to the delivery tube 9 for the radial sealing with respect to the said delivery tube 9.

The opening of the aeration device 28 and of the sealing space for the release of the outer aeration openings 39 takes place when the nebuliser 1 is primed corresponding to the ninth embodiment. During tensioning, the actuating part 52 is displaced axially against the force of the spring element 50 and the seal 49 is thereby retracted axially from the counter-seal 55. In the primed state, the spring element 50 then effects a re-closure. Thus, in the eleventh embodiment, an only temporary opening of the aeration device 28 again takes place, namely preferably, exclusively during the withdrawal of fluid.

Figure 19:
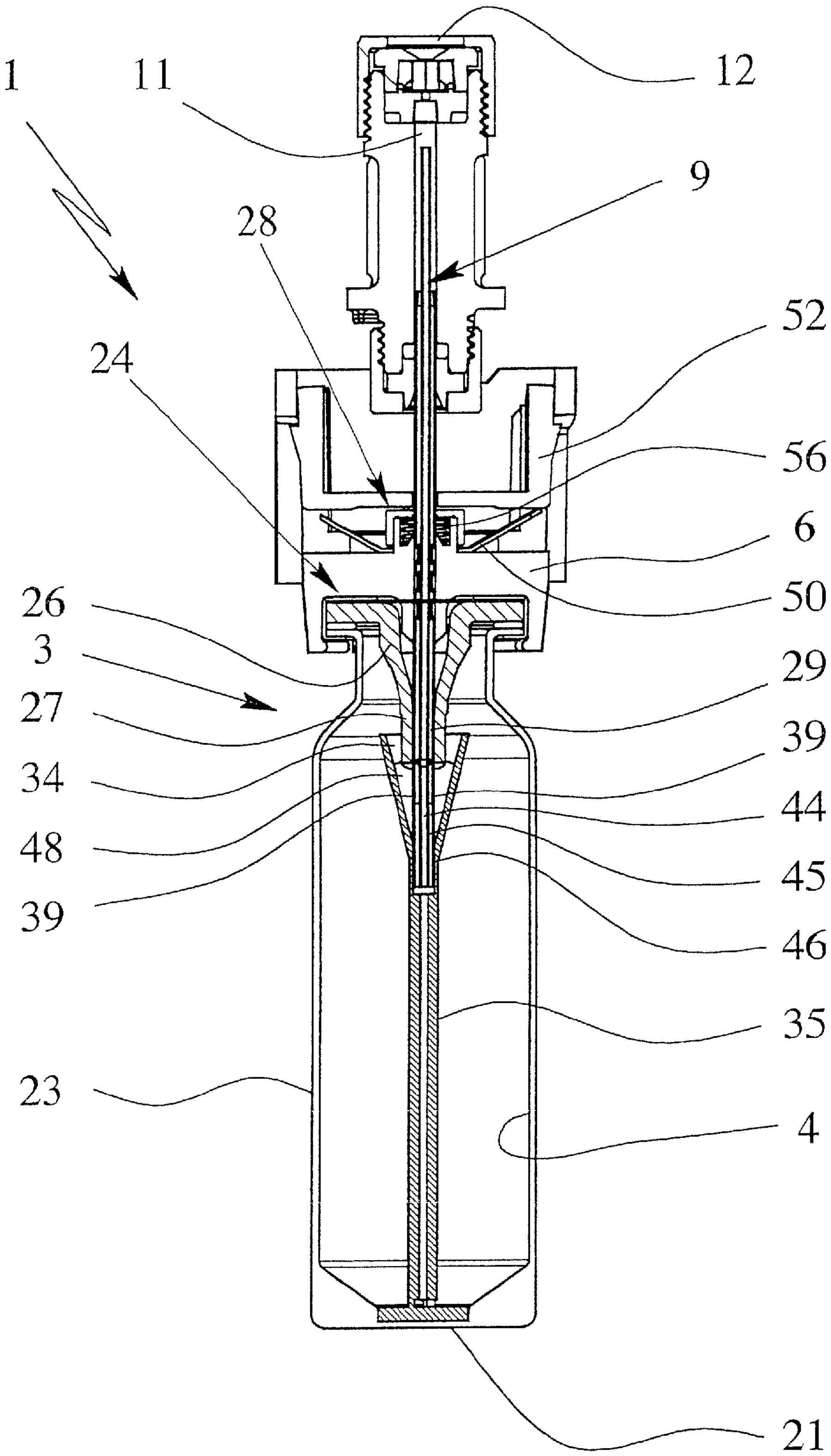
FIG. 19 is a diagrammatic sectional view of a proposed container and of parts of the proposed nebuliser according to a twelfth embodiment.
Figure 20:
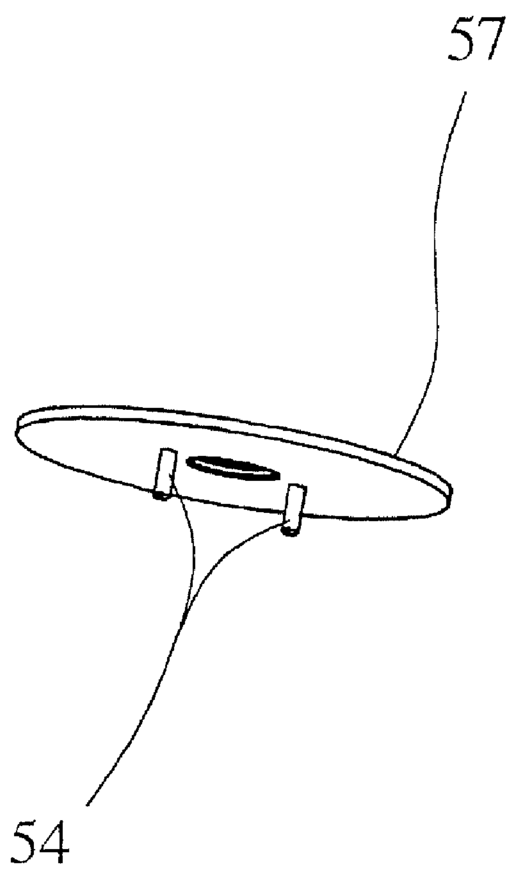
FIG. 20 is an enlarged diagrammatic sectional view of a part of the nebuliser according to FIG. 19.

FIG. 19 shows a diagrammatic sectional view of a twelfth embodiment of the nebuliser 1 according to the invention (only in part) and of the container 3. In the twelfth embodiment, a spring 56 is arranged in a receiving space and tensions a seal (not shown) in the closed and sealing position against the outer aeration opening(s) 39 of the delivery tube 9. The actuating part 52 is, corresponding to the ninth and eleventh embodiments, axially displaceable against the force of the spring element 50 during the tensioning procedure, so that at least a projection 54 arranged on the actuating part 52 or on an associated disc 57 (shown individually enlarged in FIG. 20) can axially engage in the receiving space of the spring 56 and can deform or retract the seal (not shown) in such a way that the aeration openings 39 are freed, i.e., the aeration device 28 is opened. In the twelfth embodiment, again preferably, an only temporary opening of the aeration device 28 is envisaged, in particular, exclusively during the tensioning procedure.

Figure 21:
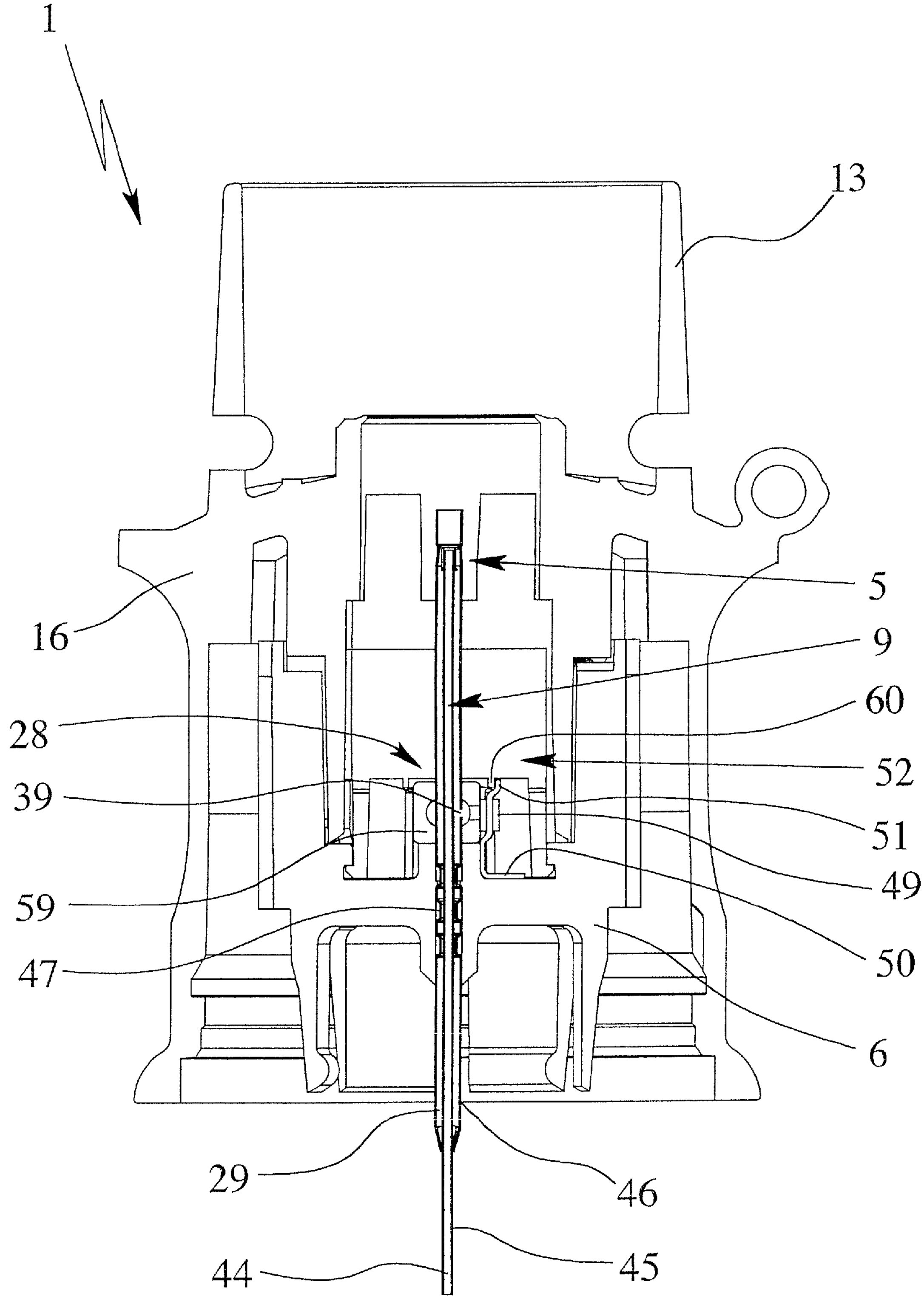
FIG. 21 is a diagrammatic sectional view of a part of a proposed nebuliser according to a thirteenth embodiment.
Figure 22:
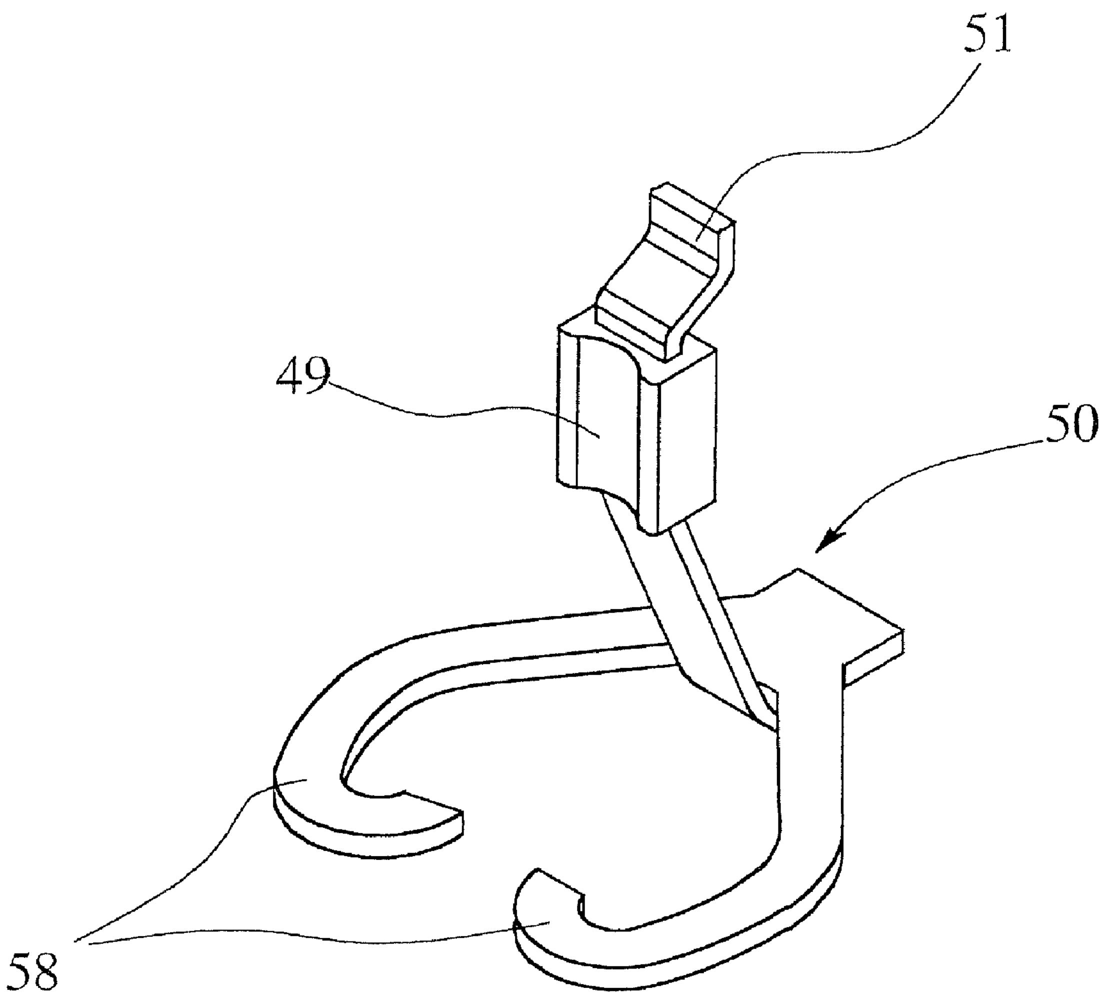
FIG. 22 is a perspective view of a spring element of the nebuliser according to FIG. 21.

FIG. 21 shows a diagrammatic sectional view of a thirteenth embodiment of the nebuliser 1 according to the invention (only in part), without an associated container 3. In the thirteenth embodiment, the aeration device 28 comprises a spring element 50, preferably, configured according to FIG.

22 and with an actuating arm 51 carrying the seal 49 and with at least one holding section 58 for securing the spring element 50 to the delivery tube 9, the holder 6 and/or to another suitable part of the nebuliser 1.

The actuating arm 51 can be elastically radially deflected and has a free end projecting axially beyond the seal 49. When the aeration device 28 is closed, the seal 49 seals off the aeration opening 39, in particular, by radially bearing against it, in which the seal 49 either covers and seals the associated aeration opening 39 directly, or does so only indirectly by bearing against a non-rigid intermediate part 59, illustrated in FIG. 21, that surrounds the aeration opening 39.

Figure 23:
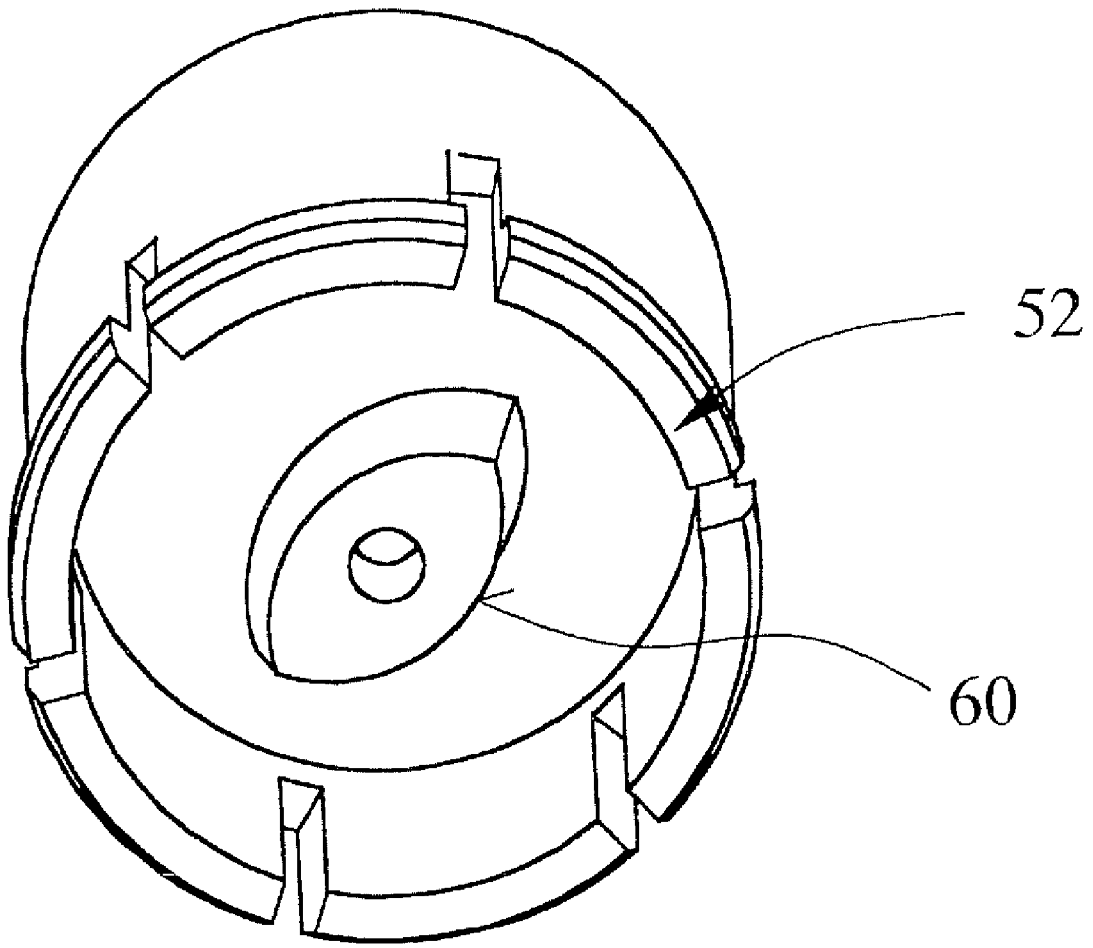
FIG. 23 shows a lower view of an actuating part of the nebuliser according to FIG. 21.

Furthermore, the aeration device 28 includes the actuating part 52, which, in the thirteenth embodiment, comprises a bearing curve 60 for the actuating arm 51. FIG. 23 shows in an enlarged lower view the actuating part 52 with the bearing curve 60. The actuating part 52 is arranged on the side of the holder 6 facing away from the container 3 (not shown here), and in particular, engages therein. The actuating part 6 can, during the tensioning process, rotate relative to the spring element 50 on account of a corresponding radial projection or the like (not shown in more detail), so that the actuating arm 51, lying with its free end against the bearing curve 60, can be deflected from the bearing curve 60 in such a way that the seal 49 can be raised, in particular, radially from the aeration opening 39 or at least from the intermediate part 59, so as to open the aeration device 28. After the tensioning, a closure and sealing of the aeration opening(s) 39 by the seal 49 again takes place on account of the corresponding shape of the bearing curve 60 and/or on account of the restoring force of the spring element 50 and actuating arm 51. If necessary, the actuating arm 51 may also be forcibly moved by the actuating part 52.

Consequently, in the thirteenth embodiment, preferably, also only a temporary opening is envisaged, in particular, only during the tensioning procedure and withdrawal of fluid. However, other opening times and/or durations are also feasible and a permanent opening of the aeration device 28—in particular, by a suitably altered bearing curve 60—can be realized.

It is obvious that other structural solutions for the temporary release of the outer aeration openings 39 and of the channel 29 are also possible. In particular, other valves or the like may also be used for this purpose.

Figure 24:
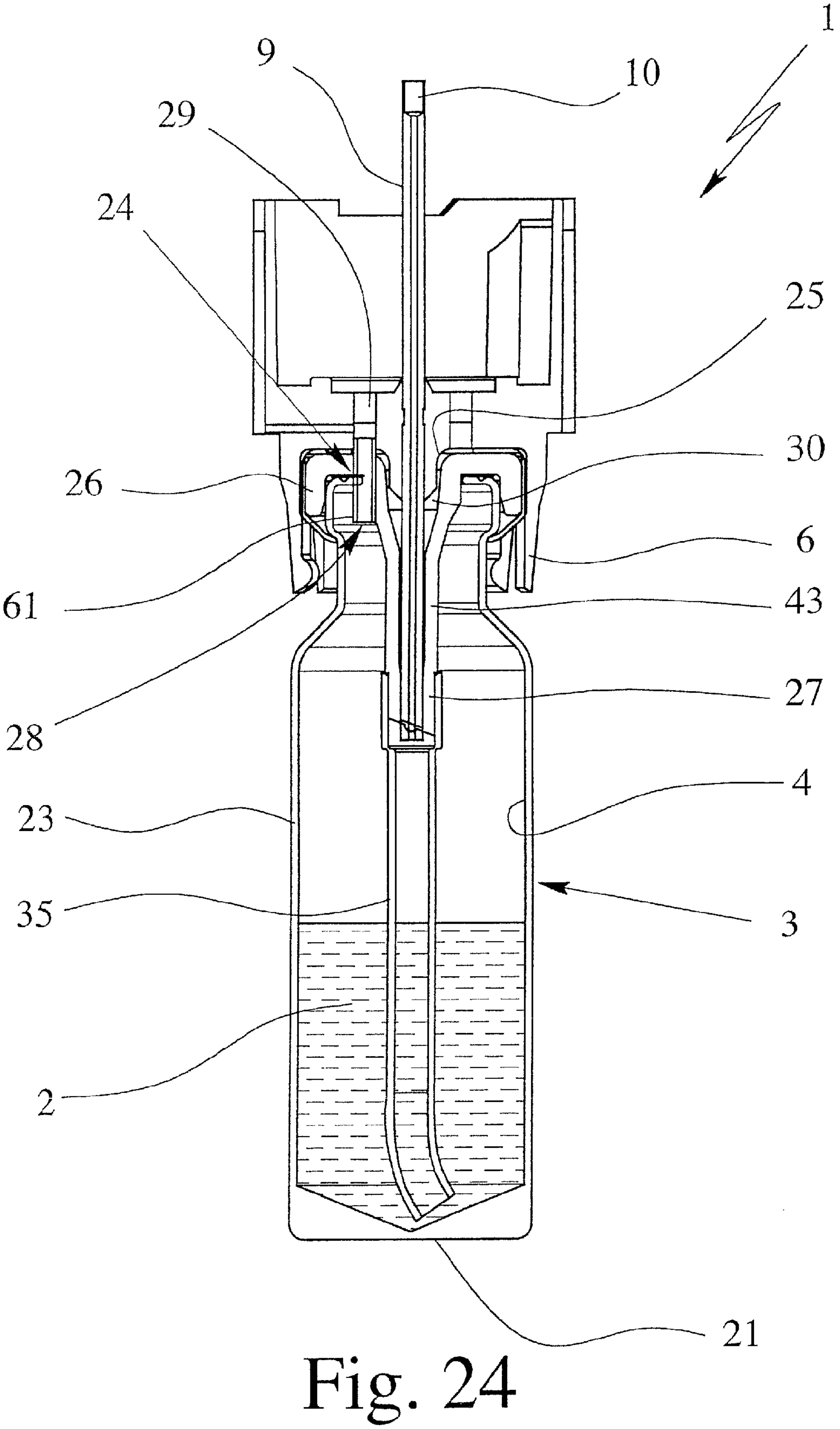
FIG. 24 is a diagrammatic sectional view of a proposed container and of parts of the proposed nebuliser according to a fourteenth embodiment.

FIG. 24 shows in a diagrammatic sectional view a fourteenth embodiment of the nebuliser 1 according to the invention (only in part) and of the container 3. In the fourteenth embodiment, the nebuliser 1, in particular, the holder 6 for the container 3, comprises in addition to the delivery element or delivery tube 9, a second, in particular, tubular connecting element 61, which on insertion of the delivery tube 9 into the container 3 simultaneously engages, in particular, in parallel, in a corresponding opening of the closure 24 or the like and forms a gas connection for the aeration of the fluid space 4. In particular, the connecting element 61 forms a channel 29 of the aeration device 28 that continues into the holder 6 and is, preferably, dimensioned corresponding to the first to fifth embodiments in order, on the one hand, to allow a rapid pressure compensation, and on the other hand, to permit only slight losses of fluid 2 by diffusion, evaporation or the like. The channel 29 or the connecting element 61 is, preferably, in turn, provided on the fluid side or on the side of the fluid space 4 with the semi-permeable element 34 which, however, is not shown in FIG. 24 for reasons of clarity.

Preferably, the connecting element 61 is adequately sealed with respect to the closure 24, for example, corresponding to the delivery tube 9, in order to minimise the losses of fluid by diffusion, evaporation or the like.

According to a variant (not shown), the connecting element 61 and the channel 29 for aeration and de-aeration may also be formed separately from the holder 6 by another part of the nebuliser 1 and/or may engage independently of the closure 24 on the container 3, in particular, if necessary, on the base side. The container base 21 is then preferably provided with a corresponding suitable base element or the like.

The possibly only temporary opening of the aeration device 28 may—as already explained on the basis of the various embodiments—take place through and/or during a movement of the delivery element, in particular, delivery tube 9, relative to the container 3. Alternatively or in addition, this may also involve a movement of the holder 6 and/or of the inner part 17 relative to the container 3, or may involve a movement of the container 3 relative to another part of the nebuliser 1. The movement may, in particular, serve for fluid removal, fluid delivery, pressure generation and/or atomization. In particular, the movement may be a translational and/or rotational and/or superimposed and/or stroke-like movement. The movement may, as already mentioned, lead to an initial opening of the container 3 or closure 24 and/or to an initial or temporary opening of the aeration device 28.

According to a further variant (not shown), the nebuliser 1 and container 3 may, in addition to the aeration device 28, which is designed for a rapid pressure compensation, also comprise a pressure compensation device (not shown) for a slow pressure compensation, in particular, when the aeration device 28 is closed, and/or for pressure compensation in the case of changes in temperature or ambient pressure. The pressure compensation device may, optionally, also be designed as a valve that preferably opens when a specific pressure difference is exceeded.

In general it should be mentioned that with the nebuliser 1 according to the invention the container 3 can preferably be inserted, i.e., can be incorporated into the nebuliser 1. Consequently, the container 3 is, preferably, a separate structural part. However, the container 3 may, in principle, also be formed directly by the nebuliser 1 or by a structural part of the nebuliser 1, or may be integrated in some other way into the nebuliser 1.

The container 3 is, preferably, sterile or sterilisable. Particularly preferably, the closed container 3 is designed to be suitably temperature-resistant. In addition, the closure 24 maintains the container 3, preferably, sterile.

As already mentioned, individual features, aspects and/or principles of the aforedescribed embodiments may also be arbitrarily combined with one another and in particular, in the known nebuliser according to FIGS. 1 & 2, though such features, etc. may also be employed in similar or other nebulisers.

In contrast to fixed equipment or the like, the nebuliser 1 according to the invention is, preferably, designed to be transportable, and in particular, is a mobile hand-held device.

The solution according to the invention may, however, be employed not only in the individual nebulisers 1 described herein, but also in other nebulisers or inhalers, for example, powder inhalers or so-called "metered dose inhalers".

Particularly preferably, the nebuliser 1 is designed as an inhaler, in particular, for medical aerosol treatment. Alternatively, the nebuliser 1 may, however, also be designed for other purposes, preferably, for the atomization of a cosmetic fluid, and may, in particular, be designed as a perfume or fragrance atomizer. The container 3 accordingly contains, for example, a medicament formulation or a cosmetic liquid, such as perfume or the like.

Preferably, the fluid 2 is a liquid, as already mentioned, in particular, an aqueous or ethanolic medicament formulation. However, it may also be another medicament formulation, a suspension or the like, or also a particulate composition or powder.

Preferred constituents and/or formulations of the preferably medicinal fluid are listed hereinafter. As already mentioned, these may be aqueous or non-aqueous solutions, mixtures, ethanol-containing or solvent-free formulations or the like. The fluid 2, particularly preferably, contains the following:

All inhalable compounds, for example, also inhalable macromolecules, as disclosed in EP 1 003 478, are used as pharmaceutically active substances, substance formulations or substance mixtures. Preferably, substances, substance formulations or substance mixtures that are used for inhalation purposes are employed to treat respiratory pathway conditions.

Particularly preferred in this connection are medicaments that are selected from the group consisting of anticholinergic agents, betamimetics, steroids, phosphodiesterase IV inhibitors, LTD4 antagonists and EGFR kinase inhibitors, antiallergic agents, ergot alkaloid derivatives, triptanes, CGRP antagonists, phosphodiesterase V inhibitors, as well as combinations of such active substances, e.g. betamimetics plus anticholinergic agents or betamimetics plus antiallergic agents. In the case of combinations at least one of the active constituents contains preferably chemically bound water. Anticholinergic agent-containing active substances are preferably used, as single preparations or in the form of combination preparations.

The following, in particular, may be mentioned as examples of effective constituents or their salts:

Anticholinergic agents are preferably selected from the group consisting of tiotropium bromide, oxitropium bromide, flutropium bromide, ipratropium bromide, glycopyrronium salts, trospium chloride, tolterodine, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, cyclopropyltropine methyl 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide and scopine 9-hydroxymethyl-xanthene-9-carboxylate methobromide, optionally in the form of their racemates, enantiomers or diastereomers, and optionally in the form of their solvates and/or hydrates.

Betamimetics which may be used are preferably selected from among albuterol, bambuterol, bitolterol, broxaterol, carbuterol, clenbuterol, fenoterol, formoterol, hexoprenaline, ibuterol, indacaterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzolsulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]-sulphonyl}ethyl]-amino}ethyl]-2(3H)-benzothiazolone, 1-(2-fluoro-4-hydroxy-phenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1.4-benzoxazin-8-yl]-2-[3-(4-methoxyphenyl)-2-methyl-2-propylamino]ethanol, 1-[2H-5-hydroxy-3-oxo-4H-1.4-benzoxazin-8-yl]-2-[3-(4-n-butyloxyphenyl)-2-methyl-2-propylamino]ethanol, 1-[2H-5-hydroxy-3-oxo-4H-1.4-benzoxazin-8-yl]-2-{4-[3-(4-methoxyphenyl)-1.2.4-triazol-3-yl]-2-methyl-2-butylamino}ethanol, 5-hydroxy-8-(1-hydroxy-2-isopropylaminobutyl)-2H-1.4-benzoxazin-3-(4H)-one, 1-(4-amino-3-chloro-5-trifluormethylphenyl)-2-tert.-butylamino)ethanol and 1-(4-ethoxycarbonyl-amino-3-cyano-5-fluorophenyl)-2-(tert.-butylamino)ethanol, optionally in the form of the racemates, enantiomers or diastereomers thereof and optionally in the form of the pharmacologically acceptable acid addition salts, solvates and/or hydrates thereof.

Steroids which may be used are preferably selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl 6a,9a-difluoro-17a-[(2-furanylcarbonyl)oxy]-11b-hydroxy-16a-methyl-3-oxo-androsta-1,4-diene-17b-carbothionate, (S)-(2-oxo-tetrahydro-furan-3S-yl) 6a,9a-difluoro-11b-hydroxy-16a-methyl-3-oxo-17a-propionyloxy-androsta-1,4-diene-17b-carbothionate and etiprednol-dichloroacetate (BNP-166), optionally in the form of the racemates, enantiomers or diastereomers thereof, and optionally, in the form of the salts and derivatives thereof, the solvates and/or hydrates thereof.

PDE IV-inhibitors which may be used are preferably selected from among enprofyllin, theophyllin, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropylmethoxybenzamide, NCS-613, pumafentine, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]

acetate, (S)-(−)-ethyl[4-(3-cyclopentyloxy-4-methoxyphenyl)pyrrolidin-2-ylidene]acetate, CDP840, Bay-198004, D-4418, PD-168787, T-440, T-2585, arofyllin, atizoram, V-11294A, Cl-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridin, optionally in the form of the racemates, enantiomers or diastereomers thereof and optionally in the form of the pharmacologically acceptable acid addition salts, solvates and/or hydrates thereof.

LTD4-antagonists which may be used are preferably selected from among montelukast, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3 (3-(2-(2,3-dichlorothieno[3,2-b]pyridin-5-yl)-(E)-ethenyl)phenyl)-3-(2-(1-hydroxy-1-methyl-ethyl)phenyl)propyl)thio)methyl)cyclopropane-acetic acid, pranlukast, zafirlukast, [2-[[2-(4-tert-butyl-2-thiazolyl)-5-benzofuranyl]oxymethyl]phenyl]acetic acid, MCC-847 (ZD-3523), MN-001, MEN-91507 (LM-1507), VUF-5078, VUF-K-8707 and L-733321, optionally in the form of the racemates, enantiomers or diastereomers thereof optionally in the form of the pharmacologically acceptable acid addition salts thereof and optionally in the form of the salts and derivatives thereof, the solvates and/or hydrates thereof.

EGFR-kinase inhibitors which may be used are preferably selected from among cetuximab, trastuzumab, ABX-EGF, Mab ICR-62, 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)-amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)-methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts thereof, the solvates and/or hydrates thereof.

By acid addition salts, salts with pharmacologically acceptable acids which the compounds may possibly be capable of forming are meant, for example, salts selected from among the hydrochloride, hydrobromide, hydriodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-tolenesulphonate, preferably hydrochloride, hydrobromide, hydrosulphate, hydrophosphate, hydrofumarate and hydromethanesulphonate.

Examples of antiallergics are: disodium cromoglycate, nedocromil.

Examples of derivatives of the ergot alkaloids are: dihydroergotamine, ergotamine.

For inhalation, it is possible to use medicaments, medicament formulations and mixtures including the abovementioned active constituents, as well as their salts, esters and combinations of these active constituents, salts and esters.

What is claimed is:

1. Nebuliser for a fluid, with an insertable container having a fluid space for the fluid, wherein the container has a rigid, gas-tight outer case and a closure which hermetically seals the container in a gas-tight manner and is openable by connecting or inserting a delivery element of the nebuliser for the withdrawal of fluid from the container, the nebuliser further comprising an aeration device for aerating the container, wherein the fluid space in the container is directly aeratable, wherein the aeration device is designed for the continuous aeration of the fluid space when the closure is opened or pierced for the first time and/or after the first withdrawal of fluid by creation of a permanent opening; and wherein the aeration device is a separate part arranged under the closure of the container and having an open groove on a side of the aeration device facing the closure.

2. Nebuliser for a fluid, with an insertable container having a fluid space for the fluid, wherein the container has a rigid, gas-tight outer case and a closure which is openable by connecting or inserting a delivery element of the nebuliser for the withdrawal of fluid from the container, the nebuliser further comprising an aeration device for aerating the container, wherein the fluid space in the container is directly aeratable, wherein at least one of the container and the delivery element execute a stroke-like movement relative to each other during the withdrawal of fluid from the container and atomization of the fluid, the aeration device being opened during said stroke-like movement in a manner creating a fluidic connection between an inner fluid space of the container and the surrounding environment in which it is located, and wherein the aeration device comprises an open groove on a side of the aeration device facing the closure.

3. Nebuliser according to claim 2, wherein the aeration device is temporarily opened during said stroke-like movement.

4. Nebuliser according to claim 1, wherein the nebuliser is designed in such a way that the aeration device is opened by a movement and/or only during a movement of the delivery element, of a holder of the container, of an inner part of the nebuliser and/or of another part of the nebuliser relative to the container, wherein the inner part can move relative to the container for fluid withdrawal, fluid delivery, pressure generation and/or atomization.

5. Nebuliser according to claim 2, wherein the movement is at least one of translation and rotational.

6. Nebuliser according to claim 1, wherein the aeration device is designed in such a way that it is opened by the connection or introduction of the delivery element.

7. Nebuliser according to claim 1, wherein the aeration device is designed in such a way that the fluid space is aerated and de-aerated independently of the position of the container.

8. Nebuliser according to claim 1, wherein the outer case is made exclusively of one of glass, metal and gas-tight plastics material.

9. Nebuliser according to claim 1, wherein the fluid is filled directly into the outer case or is in contact therewith.

10. Nebuliser according to claim 1, wherein the fluid space is not deflatable.

11. Nebuliser according to claim 1, wherein the closure forms a cap of the container and/or comprises an insert that is inserted into the outer case.

12. Nebuliser according to claim 1, wherein the closure comprises a sealing element for the delivery element, wherein the delivery element penetrates the sealing element when the container or closure is open.

13. Nebuliser according to claim 1, wherein the closure comprises a sealing element; and wherein the closure has a gas-tight cover or seal.

14. Nebuliser according to claim 13, wherein the closure comprises a sealing element; wherein the delivery element penetrates the sealing element when the container or closure is open; and wherein the aeration device comprises a channel that connects the fluid space to a space between the sealing element and the cover or seal.

15. Nebuliser according to claim 1, wherein the aeration device comprises a channel with a mean or hydraulic diameter of 0.01 mm to 1 mm.

16. Nebuliser according to claim 14, wherein the channel surrounds the delivery element or an insertion opening for the delivery element in one of an annular, spiral, meandering and zigzag manner.

17. Nebuliser according to claim 14, wherein the length of the channel is between 10 times and 1000 times a diameter of the channel.

18. Nebuliser according to claim 14, wherein the channel is arranged or formed at least in sections between a cap or insert of the closure and a cover or seal of the closure.

19. Nebuliser according to claim 2, wherein the aeration device comprises a valve integrated in the closure.

20. Nebuliser according to claim 19, wherein the valve is opened by movement of at least one of the container, the delivery element, an associated holder and another part of the nebuliser.

21. Nebuliser according to claim 19, wherein the valve is opened by one of the delivery element and a holder for the container in the nebuliser.

22. Nebuliser for a fluid, with an insertable container having a fluid space for the fluid, wherein the container has a rigid, gas-tight outer case and a closure which is openable by connecting or inserting a delivery element of the nebuliser for the withdrawal of fluid from the container, the nebuliser further comprising an aeration device for aerating the container, wherein the fluid space in the container is directly aeratable, wherein the aeration device comprises a bypass on the delivery element that is formed by a longitudinally or helically running flute, groove or flat section in the exterior surface of the delivery element which forms an aerating connection between an insertion region or space of the closure and the fluid space in the container only when the aeration device is open.

23. Nebuliser according to claim 22, wherein the aeration device comprises at least one aeration opening on a side of the nebuliser which can be opened and closed by means of a seal.

24. Nebuliser according to claim 23, wherein the seal is opened by the movement of at least one of the container, the delivery element, an associated holder and another part of the nebuliser.

25. Nebuliser according to claim 1, wherein the container comprises a dip tube onto which tube the delivery element can be connected during insertion into or connection onto the closure.

26. Nebuliser according to claim 1, wherein the aeration device comprises, in addition to the delivery element, a tubular connecting element that can be inserted into or connected onto the container or closure for the aeration.

27. Nebuliser according to claim 2, wherein the aeration device comprises a semi-permeable element that is impermeable to liquid but is permeable to gases and is arranged on the fluid side with respect to said groove, a connected valve or bypass of the aeration device.

28. Nebuliser according to claim 1, wherein at least one of the container and the aeration device can be opened exclusively by at least one of mechanical action and manual actuation.

29. Nebuliser according to claim 2, wherein the aeration device has dimensions and flow resistances such that, during and/or after the withdrawal of fluid, the pressure is rapidly compensated with a half-life time of at most 60 seconds for a pressure compensation of 20 hPa.

30. Nebuliser according to claim 1, wherein the closure comprises a sealing element and a gas-tight cover, and wherein the delivery element penetrates the sealing element and the gas-tight cover when the closure is opened and wherein the groove of the aeration device connects the fluid space to a space between the sealing element and the cover even when the sealing element and the cover are closed.

31. Nebuliser according to claim 2, wherein the closure comprises a sealing element and a gas-tight cover, and wherein the delivery element penetrates the sealing element and the gas-tight cover when the closure is opened and wherein the groove of the aeration device connects the fluid space to a space between the sealing element and the cover even when the sealing element and the cover are closed.

32. Nebuliser according to claim 1, wherein the aeration device comprises a bypass on the delivery element that is formed by a longitudinally or helically running flute, groove or flat section on the exterior of the delivery element which forms a connection between an insertion region or space of the closure and the fluid space in the container when the aeration device is open.

33. Nebuliser according to claim 2, wherein the aeration device comprises a bypass on the delivery element that is formed by a longitudinally or helically running flute, groove or flat section on the exterior of the delivery element which forms a connection between an insertion region or space of the closure and the fluid space in the container when the aeration device is open.

34. Nebuliser according to claim 1, wherein the container and the delivery element execute a stroke-like movement during the withdrawal of fluid from the container, pressure generation, and pressurization and atomization of the fluid.

35. Nebuliser according to claim 2, wherein the aeration device is arranged on the nebuliser separately from the container.

36. Nebuliser according to claim 2, wherein the outer case is made exclusively of one of glass, metal and gas-tight plastics material.

37. Nebuliser according to claim 2, wherein the fluid is filled directly into the outer case or is in contact therewith.

38. Nebuliser according to claim 2, wherein the fluid space is not deflatable.

39. Nebuliser according to claim 2, wherein the closure forms a cap of the container and/or comprises an insert that is inserted into the outer case.

40. Nebuliser according to claim 2, wherein the closure comprises a sealing element for the delivery element, wherein the delivery element penetrates the sealing element when the container or closure is open.

41. Nebuliser according to claim 2, wherein the closure comprises a sealing element; and wherein the closure has a gas-tight cover or seal.

42. Nebuliser according to claim 22, wherein the aeration device is arranged on the nebuliser separately from the container.

43. Nebuliser according to claim 22, wherein the outer case is made exclusively of one of glass, metal and gas-tight plastics material.

44. Nebuliser according to claim 22, wherein the fluid is filled directly into the outer case or is in contact therewith.

45. Nebuliser according to claim 22, wherein the fluid space is not deflatable.

46. Nebuliser according to claim 22, wherein the closure forms a cap of the container and/or comprises an insert that is inserted into the outer case.

47. Nebuliser according to claim 22, wherein the closure comprises a sealing element for the delivery element, wherein the delivery element penetrates the sealing element when the container or closure is open.

48. Nebuliser according to claim 22, wherein the closure comprises a sealing element; and wherein the closure has a gas-tight cover or seal.

49. Nebuliser according to claim 1, wherein the groove has a substantially half-circular shape.

50. Nebuliser according to claim 1, wherein the groove extends at least essentially in one plane.

51. Nebuliser according to claim 1, wherein the groove is at least essentially formed between the closure and the cover or seal.

52. Nebuliser according to claim 13, wherein the cover or seal is hot-sealed or welded to the closure.

53. An insertable container for a nebuliser, comprising:

a rigid, gas-tight outer case containing a fluid space for a fluid, a closure, having a cap and an insert, which hermetically seals the container in a gas-tight manner and which is openable by connecting or inserting a delivery element of a nebuliser for the withdrawal of fluid from the container, and an aeration device for directly aerating said fluid space, wherein the aeration device comprises an arcuate section formed by a channel in a top surface of the insert, an axial section extending through the insert so as to form a connection to said fluid and a radial section formed by said channel in the top surface of the insert, the radial section connecting said arcuate section with said axial section.

54. The insertable container according to claim 53, wherein the cover is sealed to the outer case in a gas-tight manner.

55. The insertable container according to claim 53, wherein the arcuate section of the aeration device has a substantially half-circular shape.

56. The insertable container according to claim 53, wherein the insert is provided with a tubular passage and a septum or membrane attached to the tubular passage which radially seals against a delivery element upon introduction thereof through the tubular passage in to communication with said fluid space.

* * * * *